US005879659A

United States Patent [19]
Edwards et al.

[11] Patent Number: 5,879,659
[45] Date of Patent: Mar. 9, 1999

[54] TERNARY RADIOPHARMACEUTICAL COMPLEXES

[75] Inventors: David Scott Edwards, Burlington; Shuang Liu, Chelmsford, both of Mass.

[73] Assignee: DuPont Pharmaceuticals Company, Wilmington, Del.

[21] Appl. No.: 808,699

[22] Filed: Feb. 28, 1997

Related U.S. Application Data

[60] Provisional application No. 60/013,360 Mar. 13, 1996.
[51] Int. Cl.$^6$ ............ A61K 51/00; A61K 38/12; A61M 36/14; C07F 5/00
[52] U.S. Cl. ............ 424/1.69; 424/1.65; 534/10; 534/14; 530/317; 514/9; 514/11
[58] Field of Search ................ 424/1.11, 1.49, 424/1.53, 1.65, 1.69, 9.1; 206/223, 569, 570; 534/10–16, 7; 530/300, 317, 324–330; 514/9, 11

[56] References Cited

U.S. PATENT DOCUMENTS

| | | | |
|---|---|---|---|
| 4,578,079 | 3/1986 | Ruoslahti et al. | 623/11 |
| 5,066,789 | 11/1991 | Srinivasan et al. | 530/388 |
| 5,206,370 | 4/1993 | Schwartz et al. | 546/281 |
| 5,300,278 | 4/1994 | Pasqualini et al. | 534/14 |
| 5,350,837 | 9/1994 | Bridger et al. | 534/14 |
| 5,384,309 | 1/1995 | Barker et al. | 514/11 |
| 5,493,007 | 2/1996 | Burnier et al. | 530/317 |
| 5,521,156 | 5/1996 | Owen et al. | 514/11 |

FOREIGN PATENT DOCUMENTS

| | | |
|---|---|---|
| 89 08657 | 9/1989 | WIPO . |
| 9307170 | 4/1993 | WIPO . |
| 9422494 | 10/1993 | WIPO . |

OTHER PUBLICATIONS

D.A. Pearson, J. Lister–James, W.J. McBride, D.M. Wilson, L.J. Martel, E.R. Civitello and R.T. Dean, *J. Med. Chem.* 1996, 39, 1372–1382, "Thrombus Imaging Using Technetium 99m–Labeled High–Potency GPIIb/IIIa Receptor Antagonists. Chemistry and Initial Biological Studies."

S. Liu, D.S. Edwards, R.J. Looby, A.R. Harris, M.J. Poirier, J.A. Barrett, S.J. Heminway & T.R. Carroll, *Bioconjugate Chemistry,* 1995, 7, 63–71, "Labeling a Hydrazino Nicotinamide–Modified Cyclic IIb/IIIa Receptor Antagonist with 99m Tc Using Aminocarboxylates as Coligands."

*Primary Examiner*—Jose' G. Dees
*Assistant Examiner*—Michael G. Hartley
*Attorney, Agent, or Firm*—G. Jess Boudreaux; David H. Vance

[57] ABSTRACT

This invention relates to novel radiopharmaceuticals which are useful as imaging agents for the diagnosis of cardiovascular disorders, infectious disease and cancer, and to kits useful for their preparation. The radiopharmaceuticals of this invention are comprised of a transition metal radionuclide, a transition metal chelator, a biologically active group connected to said chelator, a first ancillary ligand, a second ancillary ligand capable of stabilizing the radiopharmaceutical, optionally having a linking group between said chelator and said biologically active group. Preferred radiopharmaceuticals of this invention have the formula:

$$[(Q)_d L_n - C_h ]_k - M_t (A_{L1})_y (A_{L2})_z,$$

wherein the shown variables are as defined herein.

12 Claims, 2 Drawing Sheets

TERNARY RADIOPHARMACEUTICAL COMPLEXES

This application claims the benefit of U.S. Provisional Application No. 60/013,360, filed Mar. 13, 1996.

CROSS-REFERENCE TO RELATED APPLICATIONS

The present application is related to our copending application U.S. Ser. No. 08/415,908, which is a continuation-in-part of U.S. Ser. No. 08/218,861 which is a continuation-in-part of U.S. Ser. No. 08/040,336 filed Mar. 30, 1993, the disclosures of which are incorporated herein by reference.

FIELD OF THE INVENTION

This invention relates to novel radiopharmaceuticals which are useful as imaging agents for the diagnosis of cardiovascular disorders, infectious disease and cancer, and to kits useful for their preparation. The radiopharmaceuticals are comprised of nitrogen-containing heterocycle ligated technetium-99m labeled hydrazino or diazino modified biologically active molecules that selectively localize at sites of disease and thus allow an image to be obtained of the loci using gamma scintigraphy.

BACKGROUND OF THE INVENTION

There is a current need for new methods for the non-invasive diagnosis of a variety of diseases such as thromboembolic disease, atherosclerosis, infection and cancer. Radiopharmaceuticals comprised of gamma-ray emitting radionuclide labeled biologically active molecules can fulfill the need. The biologically active molecules serve to localize the radionuclides at the sites of disease and thus allow the sites to be visualized by gamma scintigraphy. The molecules can be either proteins, antibodies, antibody fragments, peptides or polypeptides, or peptidomimetics. The molecules interact with a receptor or binding site expressed at the sites of the disease or with a receptor or binding site on an endogenous blood component, such as platelets and leukocytes, that accumulate at the sites. This interaction results in selective localization of a percentage of the injected radiopharmaceutical while the remainder is cleared either through the renal or hepatobiliary systems. The localized radiopharmaceutical is then imaged externally using gamma scintigraphy. The relative rates of sequestration, clearance and radionuclidic decay determine the ease of visualization, often expressed as the target-to-background ratio. Frequently, only certain portions of the biologically active molecules bind to the receptors; these portions are termed the recognition sequences or units.

A number of radiopharmaceuticals comprised of radionuclide labeled proteins, antibodies or antibody fragments are under development, however, to date only one has been approved by the Food and Drug Administration. This sparse record results from a combination of factors that make developing these radiopharmaceuticals difficult, including problems with manufacturing and quality control, non-optimal sequestration and clearance rates, and the occurence of antigenic or allergic responses to the radiopharmaceuticals. These problems are mainly due to the macromolecular nature of the proteins, antibodies and antibody fragments. Their high molecular weight makes direct chemical synthesis impractical, therefore they must be synthesized by recombinant or cloning techniques that typically give low yields and require extensive isolation and purification procedures. Their molecular weight can slow their rates of localization and preclude their clearance by an active elimination mechanism via the kidneys or liver, resulting in prolonged retention in the circulation which causes a high background level during imaging. Also, the body's immune system tends to recognize more efficiently larger exogenous species.

The use of lower molecular weight peptides, polypeptides or peptidomimetics as the biologically active molecules obviates a number of these problems. These molecules can be synthesized directly using classical solution chemistry or by an automated peptide synthesizer. They can be formed in higher yields and require less complicated purification procedures. They tend to clear more rapidly from the circulation by an active elimination pathway resulting in a lower background in the images. They are also usually not immunogenic. The first radionuclide labeled polypeptide radiopharmaceutical has been recently approved by the Food and Drug Administration.

There are two general methods for labeling biologically active molecules with radionuclides for use as radiopharmaceuticals termed direct and indirect labeling. Direct labeling involves attaching the radionuclide to atoms on the biologically active molecule; while the indirect method involves attaching the radionuclide via a chelator. The chelator can either be attached to the biologically active molecule prior to reaction with the radionuclide or the radionuclide labeled chelator moiety can be attached to the biologically active molecule. Several recent reviews describe these labeling methods and are incorporated herein by reference: S. Jurisson et. al., Chem. Rev., 1993, 93, 1137; A. Verbruggen, Eur. J. Nuc. Med., 1990, 17, 346; and M. Derwanjee, Semin. Nuc. Med., 1990, 20, 5.

The use of hydrazines and hydrazides as chelators to modify proteins for labeling with radionuclides has been recently disclosed in Schwartz et. al., U.S. Pat. No. 5,206, 370. For labeling with technetium-99m, the hydrazino-modified protein is reacted with a reduced technetium species, formed by reacting pertechnetate with a reducing agent in the presence of a chelating dioxygen ligand. The technetium becomes bound to the protein through what are believed to be hydrazido or diazenido linkages with the coordination sphere completed by the ancillary dioxygen ligands. Examples of ancillary dioxygen ligands include glucoheptonate, gluconate, 2-hydroxyisobutyrate, and lactate.

Certain dioxygen ligands have been recently reported to be particularly advantageous for labeling hydrazino-modified proteins with technetium-99m. Bridger et. al., U.S. Pat. No. 5,350,837, disclose a series of functionalized aminocarboxylates the use of which are reported to improve the labeling process of hydrazino-modified macromolecules such as monoclonal antibodies. The improvements are manifest by shorter reaction times and higher specific activities. Examples of these improved dioxygen ligands include hydroxyalkyl substituted glycine derivatives such as tricine.

In co-pending U.S. Ser. No. 08/218,861 (equivalent to WO 94/22494), filed Mar. 28, 1994, the synthesis of novel} radiolabeled platelet IIb/IIIa receptor antagonists as imaging agents for thromboembolic disorders is disclosed. These reagents comprise radionuclide labeled chelator modified cyclic compounds. A preferred chelator for modifying the cyclic compounds is the hydrazino or diazenido moiety. The preferred reagents are used to synthesize binary complexes comprised of the hydrazido or diazenido moiety and one of a series of ancillary ligands.

SUMMARY OF THE INVENTION

This invention provides novel radiopharmaceuticals which are useful as imaging agents for the diagnosis of cardiovascular disorders, such as thromboembolic disease or atherosclerosis, infectious disease and cancer. The radiopharmaceuticals are comprised of nitrogen-containing heterocycle ligated technetium-99m labeled hydrazino or diazenido modified biologically active molecules that selectively localize at sites of disease and thus allow an image to be obtained of the loci using gamma scintigraphy. The invention also provides methods of using said radiopharmaceuticals as imaging agents for the diagnosis of cardiovascular disorders, such as thromboembolic disease or atherosclerosis, infectious disease and cancer. It further provides kits for the preparation of said radiopharmaceuticals.

DETAILED DESCRIPTION OF THE INVENTION

Figure 1A:
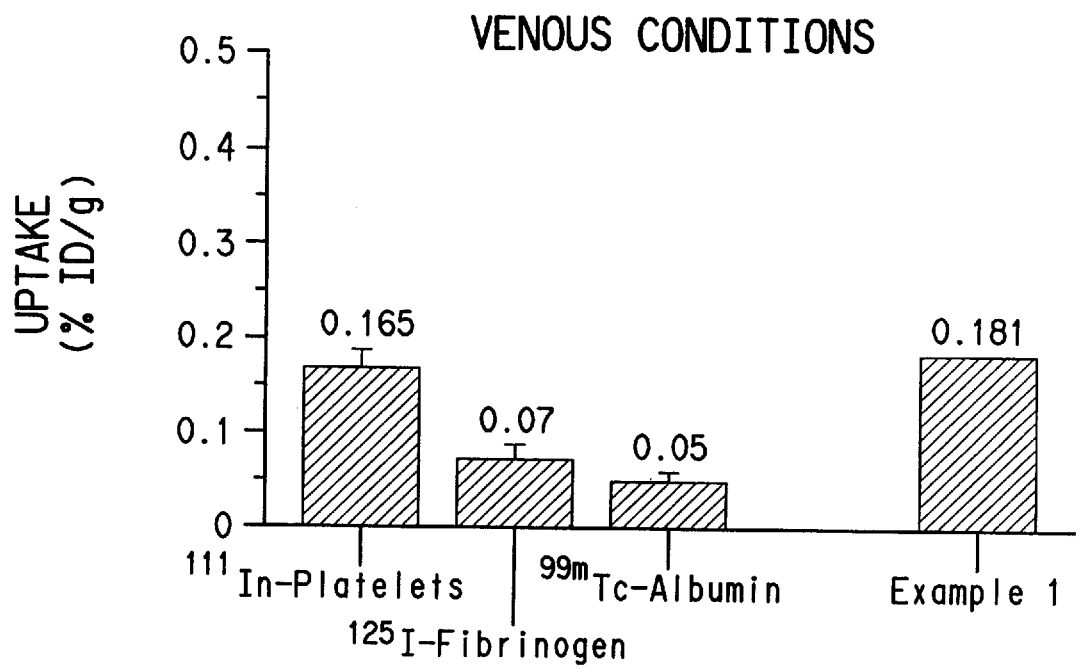
FIG. 1. Data from the Canine Arteriovenous Shunt model for the Radiopharmaceutical of Example 1 (150 $\mu$Ci/kg, i.v.), compared to $^{111}$In-platelets, $^{125}$I-fibrinogen and $^{99m}$Tc-albumin.

The present invention is directed to novel radiopharmaceuticals for the diagnosis of cardiovascular disorders, such as thromboembolic disease and atherosclerosis, infectious disease or cancer of the formula [(Q)$_{d'}$L$_n$—C$_{h'}$]$_k$—M$_t$(A$_{L1}$)$_y$(A$_{L2}$)$_z$, methods of using said radiopharmaceuticals in the diagnosis of diseases and kits useful for the preparation of said radiopharmaceutical.

[1] One embodiment of the present invention is a radiopharmaceutical comprising a first ancillary ligand, a second ancillary ligand capable of stabilizing the radiopharmaceutical, a transition metal radionuclide, a transition metal chelator, a biologically active group connected to said chelator, optionally having a linking group between said chelator and said biologically active group.

[2] Preferred radiopharmaceuticals of this invention are those having a linking group between said chelator and said biologically active group.

[3] More preferred radiopharmaceuticals of this invention are those of formula:

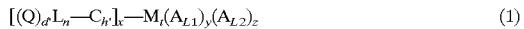

$$[(Q)_{d'}L_n\text{—}C_{h'}]_k\text{—}M_t(A_{L1})_y(A_{L2})_z \quad (1)$$

and pharmaceutically acceptable salts thereof wherein,

Q is a biologically active group;

d' is 1 to 20;

L$_n$ is a linking group of formula:

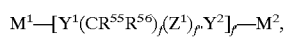

$$M^1\text{—}[Y^1(CR^{55}R^{56})_g(Z^1)_{f'}Y^2]_{f'}\text{—}M^2,$$

wherein:

$M^1$ is —[(CH$_2$)$_g$Z$^1$]$_{g'}$—(CR$^{55}$R$^{56}$)$_{g''}$—;
$M^2$ is —(CR$^{55}$R$^{56}$)$_{g''}$—[Z$^1$(CH$_2$)$_g$]$_{g'}$—;
g is independently 0–10;
g' is independently 0–1;
g'' is independently 0–10;
f is independently 0–10;
f' is independently 0–10;
f'' is independently 0–1;
$Y^1$ and $Y^2$, at each occurrence, are independently selected from:
  a bond, O, NR$^{56}$, C=O, C(=O)O, OC(=O)O, C(=O)NH—, C=NR$^{56}$, S, SO, SO$_2$, SO$_3$, NHC(=O), (NH)$_2$C(=O), (NH)$_2$C=S;
$Z^1$ is independently selected at each occurrence from a C$_6$–C$_{14}$ saturated, partially saturated, or aromatic carbocyclic ring system, substituted with 0–4 R$^{57}$; and a heterocyclic ring system, optionally substituted with 0–4 R$^{57}$;
$R^{55}$ and $R^{56}$ are independently selected at each occurrence from: hydrogen, C$_1$–C$_{10}$ alkyl substituted with 0–5 R$^{57}$, alkaryl wherein the aryl is substituted with 0–5 R$^{57}$;
$R^{57}$ is independently selected at each occurrence from the group: hydrogen, OH, NHR$^{58}$, C(=O)R$^{58}$, OC(=O)R$^{58}$, OC(=O)OR$^{58}$, C(=O)OR$^{58}$, C(=O)NR$^{58}$, C=N, SR$^{58}$, SOR$^{58}$, SO$_2$R$^{58}$, NHC(=O)R$^{58}$, NHC(=O)NHR$^{58}$, NHC(=S)NHR$^{58}$, or, alternatively, when attached to an additional molecule Q, R$^{57}$ is independently selected at each occurrence from the group: O, NR$^{58}$, C=O, C(=O)O, OC(=O)O, C(=O)N, C=NR$^{58}$, S, SO, SO$_2$, SO$_3$, NHC(=O), (NH)$_2$C(=O), (NH)$_2$C=S; and
$R^{58}$ is independently selected at each occurrence from the group: hydrogen, C$_1$–C$_6$ alkyl, benzyl, and phenyl;
x, y and z are independently 1 or 2;
$M_t$ is a transition metal radionuclide selected from the group: $^{99m}$Tc, $^{186}$Re and $^{188}$Re;
$C_{h'}$ is a radionuclide metal chelator coordinated to transition metal radionuclide $M_t$, and is independently selected at each occurrence, from the group: R$^{40}$N≡N$^+$≡, R$^{40}$R$^{41}$N—N≡, and R$^{40}$N=N(H)—; wherein
$R^{40}$ is independently selected at each occurrence from the group: a bond to L$_n$, C$_1$–C$_{10}$ alkyl substituted with 0–3 R$^{52}$, aryl substituted with 0–3 R$^{52}$, cycloalkyl substituted with 0–3 R$^{52}$, heterocycle substituted with 0–3 R$^{52}$, heterocycloalkyl substituted with 0–3 R$^{52}$, aralkyl substituted with 0–3 R$^{52}$ and alkaryl substituted with 0–3 R$^{52}$;
$R^{41}$ is independently selected from the group: hydrogen, aryl substituted with 0–3 R$^{52}$, C$_1$–C$_{10}$ alkyl substituted with 0–3 R$^{52}$, and a heterocycle substituted with 0–3 R$^{52}$;
$R^{52}$ is independently selected at each occurrence from the group: a bond to L$_n$, =O, F, Cl, Br, I, —CF$_3$, —CN, —CO$_2$R$^{53}$, —C(=O)R$^{53}$, —C(=O)N(R$^{53}$)$_2$, —CHO, —CH$_2$OR$^{53}$, —OC(=O)R$^{53}$, —OC(=O)OR$^{53a}$, —OR$^{53}$, —OC(=O)N(R$^{53}$)$_2$, —NR$^{53}$C(=O)R$^{53}$, —N(R$^{53}$)$_3$+, —NR$^{54}$C(=O)OR$^{53a}$, —NR$^{53}$C(=O)N(R$^{53}$)$_2$, —NR$^{54}$SO$_2$N(R$^{53}$)$_2$, —NR$^{54}$SO$_2$R$^{53a}$, —SO$_3$H, —SO$_2$R$^{53a}$, —SR$^{53}$, —S(=O)R$^{53a}$, —SO$_2$N(R$^{53}$)$_2$, —N(R$^{53}$)$_2$, —NHC(=NH)NHR$^{53}$, —C(=NH)NHR$^{53}$, =NOR$^{53}$, NO$_2$, —C(=O)NHOR$^{53}$, —C(=O)NHNR$^{53}$R$^{53a}$, —OCH$_2$CO$_2$H, 2-(1-morpholino)ethoxy;
$R^{53}$, $R^{53a}$, and $R^{54}$ are each independently selected at each occurrence from the group: hydrogen, C$_1$–C$_6$ alkyl, and a bond to L$_n$;

$A_{L1}$ is a first ancillary ligand selected from the group: dioxygen ligand and functionalized aminocarboxylate;

$A_{L2}$ is an ancillary ligand capable of stabilizing the radiopharmaceutical selected from the group:

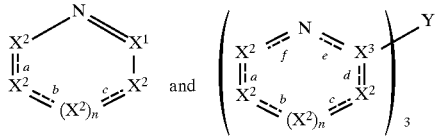

wherein n is 0 or 1;

$X^1$ is independently selected at each occurrence from the group: $CR^{64}$ and N;

$X^2$ is independently selected at each occurrence from the group: $CR^{64}$, $CR^{64}R^{64}$, N, $NR^{64}$, O and S;

$X^3$ is independently selected at each occurrence from the group: C, $CR^{64}$, and N;

provided the total number of heteroatoms in each ring of the ligand $A_{L2}$ is 1 to 4;

Y is selected from the group: $BR^{64-}$, $CR^{64}$, (P=O), (P=S);

and a, b, c, d, e and f indicate the positions of optional double bonds, provided that one of e and f is a double bond;

$R^{64}$ is independently selected at each occurrence from the group:

H, $C_1$–$C_{10}$ alkyl substituted with 0–3 $R^{65}$, $C_2$–$C_{10}$ alkenyl substituted with 0–3 $R^{65}$, $C_2$–$C_{10}$ alkynyl substituted with 0–3 $R^{65}$, aryl substituted with 0–3 $R^{65}$, carbocycle substituted with 0–3 $R^{65}$, and $R^{65}$;

or, alternatively, two $R^{64}$ may be taken together with the atom or atoms to which they are attached to form a fused aromatic, carbocyclic or heterocyclic ring, substituted with 0–3 $R^{65}$;

$R^{65}$ is independently selected at each occurrence from the group: =O, F, Cl, Br, I, —$CF_3$, —CN, —$NO_2$, —$CO_2R^{66}$, —C(=O)$R^{66}$, —C(=O)N($R^{66}$)$_2$, —N($R^{66}$)$_3$+ —$CH_2OR^{66}$, —OC(=O)$R^{66}$, —OC(=O)O$R^{66a}$, —O$R^{66}$, —OC(=O)N($R^{66}$)$_2$, —$NR^{66}$C(=O)$R^{66}$, —$NR^{67}$C(=O)O$R^{66a}$, —$NR^{66}$C(=O)N($R^{66}$)$_2$, —$NR^{67}$SO$_2$N($R^{66}$)$_2$, —$NR^{67}$SO$_2R^{66a}$, —$SO_3H$, —$SO_2R^{66a}$, —$SO_2$N($R^{66}$)$_2$, —N($R^{66}$)$_2$, —$OCH_2CO_2H$; and $R^{66}$, $R^{66a}$, and $R^{67}$ are each independently selected at each occurrence from the group: hydrogen and $C_1$–$C_6$ alkyl.

[4] Also more preferred are the radiopharmaceuticals of this invention wherein:

Q is a biologically active molecule selected from the group: IIb/IIIa receptor antagonists, IIb/IIIa receptor ligands, fibrin binding peptides, leukocyte binding peptides, chemotactic peptides, somatostatin analogs, and selectin binding peptides;

d' is 1 to 3;

$L_n$ is:

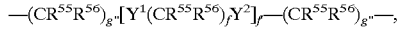

wherein:

g" is 0–5;

f is 0–5;

f' is 1–5;

$Y^1$ and $Y^2$, at each occurrence, are independently selected from:

O, $NR^{56}$, C=O, C(=O)O, OC(=O)O, C(=O)NH, C=$NR^{56}$, S, SO, $SO_2$, $SO_3$, NHC(=O), (NH)$_2$C(=O), (NH)$_2$C=S;

$R^{55}$ and $R^{56}$ are independently selected at each occurrence from:

hydrogen, $C_1$–$C_{10}$ alkyl and alkaryl;

x and y are 1;

$M_t$ is $^{99m}$Tc;

$C_{h'}$ is selected from the group: $R^{40}$N=$N^+$= and $R^{40}R^{41}$N—N=; wherein $R^{40}$ is independently selected at each occurrence from the group: aryl substituted with 0–3 $R^{52}$, and heterocycle substituted with 0–3 $R^{52}$;

$R^{41}$ is independently selected from the group: hydrogen, aryl substituted with 0–1 $R^{52}$, $C_1$–$C_3$ alkyl substituted with 0–1 $R^{52}$, and a heterocycle substituted with 0–1 $R^{52}$;

$R^{52}$ is independently selected at each occurrence from the group: a bond to $L_n$, —$CO_2R^{53}$, —$CH_2OR^{53}$, —$SO_3H$, —$SO_2R^{53a}$, —N($R^{53}$)$_2$, —N($R^{53}$)$_3$+ —NHC(=NH)$NHR^{53}$, and —$OCH_2CO_2H$;

$R^{53}$ and $R^{53a}$ are each independently selected at each occurrence from the group: hydrogen and $C_1$–$C_3$ alkyl;

$A_{L1}$ is a functionalized aminocarboxylate;

n is 0;

Y is $BR^{64-}$;

$R^{64}$ is independently selected at each occurrence from the group:

H, $C_1$–$C_3$ alkyl substituted with 0–3 $R^{65}$, aryl substituted with 0–3 $R^{65}$, and $R^{65}$;

or, alternatively, two $R^{64}$ may be taken together with the atom or atoms to which they are attached to form a fused aromatic or heterocyclic ring, substituted with 0–3 $R^{65}$;

$R^{65}$ is independently selected at each occurrence from the group: —$NO_2$, —$CO_2R^{66}$, —$OR^{66}$, —$SO_3H$, and —$OCH_2CO_2H$; and $R^{66}$ is hydrogen.

[5] Most preferred are those radiopharmaceuticals of this invention wherein:

Q is a biologically active molecule selected from the group: IIb/IIIa receptor antagonists and chemotactic peptides;

d' is 1;

$Y^1$ and $Y^2$, at each occurrence, are independently selected from:

O, $NR^{56}$, C=O, C(=O)O, OC(=O)O, C(=O)NH, C=$NR^{56}$, NHC(=O), (NH)$_2$C(=O);

$R^{55}$ and $R^{56}$ are hydrogen;

z is 1;

$R^{40}$ is heterocycle substituted with $R^{52}$;

$R^{41}$ is hydrogen;

$R^{52}$ is a bond to $L_n$;

$A_{L1}$ is tricine;

$X^2$ is independently selected at each occurrence from the group: $CR^{64}$, $CR^{64}R^{64}$, N, $NR^{64}$ and O;

$X^3$ is N;

provided the total number of heteroatoms in each ring of the ligand $A_{L2}$ is 2 to 3;

$R^{64}$ is independently selected at each occurrence from the group:

H, $C_1$–$C_3$ alkyl substituted with 0–1 $R^{65}$, aryl substituted with 0–1 $R^{65}$; and $R^{65}$;

$R^{65}$ is independently selected at each occurrence from the group: —$NO_2$, —$CO_2R^{66}$, —$OR^{66}$, and —$SO_3H$.

[6] Specifically preferred radiopharmaceuticals are those wherein:
Q is
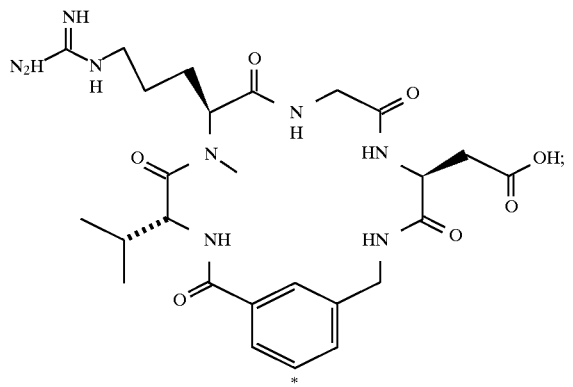
d' is 1;
$L_n$ is attached to Q at the carbon atom designated with a * and has the formula:
—(C=O)NH(CH$_2$)$_5$C(=O)NH—;
$C_{h'}$ is
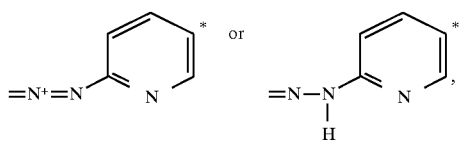
and is attached to $L_n$ at the carbon atom designated with a *;
$M_t$ is $^{99m}$Tc;
$A_{L1}$ is tricine;
x, y and z are 1;
and $A_{L2}$ is selected from the group:
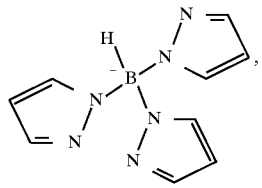
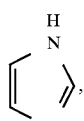
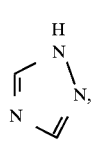
-continued
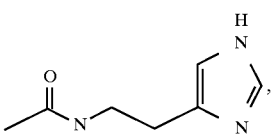
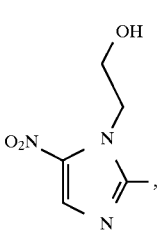
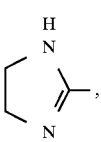
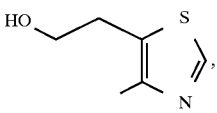
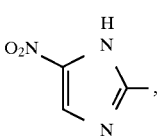
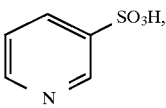
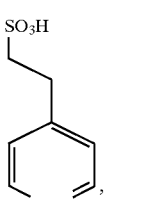
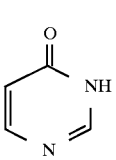
and -continued

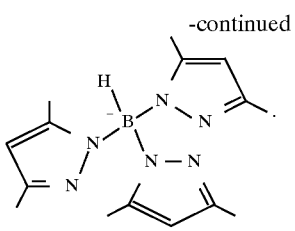

[7] Another embodiment of this invention is a method for radioimaging a mammal comprising (i) administering to said mammal an effective amount of a radiopharmaceutical of any of Claims 1–6, and (ii) scanning the mammal using a radioimaging device.

[8] Another embodiment of this invention is a method for visualizing sites of platelet deposition in a mammal by radioimaging, comprising (i) administering to said mammal an effective amount of a radiopharmaceutical of any of Claims 1–6, and (ii) scanning the mammal using a radioimaging device.

[9] Another embodiment of this invention is a method of determining platelet deposition in a mammal comprising administering to said mammal a radiopharmaceutical composition of any of Claims 1–6, and imaging said mammal.

[10] Another embodiment of this invention is a method of diagnosing a disorder associated with platelet deposition in a mammal comprising administering to said mammal a radiopharmaceutical composition of any of Claims 1–6, and imaging said mammal.

[11] Another embodiment of this invention is a kit for preparing a radiopharmaceutical comprising:

(a) a predetermined quantity of a sterile, pharmaceutically acceptable reagent of formula:

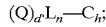

(Q)$_{d'}$L$_n$—C$_h$;

(b) a predetermined quantity of a sterile, pharmaceutically acceptable first ancillary ligand, A$_{L1}$, selected from the group:
dioxygen ligand and functionalized aminocarboxylate;

(c) a predetermined quantity of a sterile, pharmaceutically acceptable second ancillary ligand, A$_{L2}$, selected from the group:

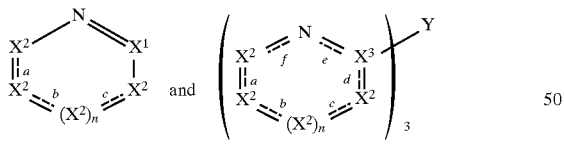

(d) a predetermined quantity of a sterile, pharmaceutically acceptable reducing agent; and (e) optionally, a predetermined quantity of one or more sterile, pharmaceutically acceptable components selected from the group: transfer ligands, buffers, lyophilization aids, stabilization aids, solubilization aids and bacteriostats;

wherein:

Q is a biologically active molecule;
d' is 1 to 20;
L$_n$ is a linking group of formula:

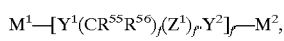

M$^1$—[Y$^1$(CR$^{55}$R$^{56}$)$_f$(Z$^1$)$_{f'}$Y$^2$]$_{f''}$—M$^2$, wherein:

M$^1$ is —[(CH$_2$)$_g$Z$^1$]$_{g'}$—(CR$^{55}$R$^{56}$)$_{g''}$—;
M$^2$ is —(CR$^{55}$R$^{56}$)$_{g''}$—[Z$^1$(CH$_2$)$_g$]$_{g'}$—;
g is independently 0–10;
g' is independently 0–1;
g" is independently 0–10;
f is independently 0–10;
f' is independently 0–10;
f" is independently 0–1;
Y$^1$ and Y$^2$, at each occurrence, are independently selected from:
a bond, O, NR$^{56}$, C=O, C(=O)O, OC(=O)O, C(=O)NH—, C=NR$^{56}$, S, SO, SO$_2$, SO$_3$, NHC(=O), (NH)$_2$C(=O), (NH)$_2$C=S;
Z$^1$ is independently selected at each occurrence from a C$_6$–C$_{14}$ saturated, partially saturated, or aromatic carbocyclic ring system, substituted with 0–4 R$^{57}$, and a heterocyclic ring system, optionally substituted with 0–4 R$^{57}$;
R$^{55}$ and R$^{56}$ are independently selected at each occurrence from:
hydrogen; C$_1$–C$_{10}$ alkyl substituted with 0–5 R$^{57}$, alkaryl wherein the aryl is substituted with 0–5 R$^{57}$;
R$^{57}$ is independently selected at each occurrence from the group: hydrogen, OH, NHR$^{58}$, C(=O)R$^{58}$, OC(=O)R$^{58}$, OC(=O)OR$^{58}$, C(=O)OR$^{58}$, C(=O)NR$^{58}$, C=N, SR$^{58}$, SOR$^{58}$, SO$_2$R$^{58}$, NHC(=O)R$^{58}$, NHC(=O)NHR$^{58}$, NHC(=S)NHR$^{58}$;
or, alternatively, when attached to an additional molecule Q, R$^{57}$ is independently selected at each occurrence from the group: O, NR$^{58}$, C=O, C(=O)O, OC(=O)O, C(=O)N, C=NR$^{58}$, S, SO, SO$_2$, SO$_3$, NHC(=O), (NH)$_2$C(=O), (NH)$_2$C=S; and,
R$^{58}$ is independently selected at each occurrence from the group: hydrogen, C$_1$–C$_6$ alkyl, benzyl, and phenyl;
C$_h$ is a radionuclide metal chelator selected from the group: R$^{40}$R$^{41}$N—N=C(C$_1$–C$_3$ alkyl)$_2$ and R$^{40}$NNH$_2$—, and R$^{40}$R$^{41}$N—N=CR$^{80}$R$^{81}$, wherein,
R$^{40}$ is independently selected at each occurrence from the group: a bond to L$_n$, C$_1$–C$_{10}$ alkyl substituted with 0–3 R$^{52}$, aryl substituted with 0–3 R$^{52}$, cycloalkyl substituted with 0–3 R$^{52}$, heterocycle substituted with 0–3 R$^{52}$, heterocycloalkyl substituted with 0–3 R$^{52}$, aralkyl substituted with 0–3 R$^{52}$ and alkaryl substituted with 0–3 R$^{52}$;
R$^{41}$ is independently selected from the group: hydrogen, aryl substituted with 0–3 R$^{52}$, C$_1$–C$_{10}$ alkyl substituted with 0–3 R$^{52}$, and a heterocycle substituted with 0–3 R$^{52}$;
R$^{52}$ is independently selected at each occurrence from the group: a bond to L$_n$, =O, F, Cl, Br, I, —CF$_3$, —CN, —CO$_2$R$^{53}$, —C(=O)R$^{53}$, —C(=O)N(R$^{53}$)$_2$, —CHO, —CH$_2$OR$^{53}$, —OC(=O)R$^{53}$, —OC(=O)OR$^{53a}$, —OR$^{53}$, —OC(=O)N(R$^{53}$)$_2$, —NR$^{53}$C(=O)R$^{53}$, —NR$^{54}$C(=O)OR$^{53a}$, —N(R$^{53}$)$_3$+, —NR$^{53}$C(=O)N(R$^{53}$)$_2$, —NR$^{54}$SO$_2$N(R$^{53}$)$_2$, —NR$^{54}$SO$_2$R$^{53a}$, —SO$_3$H, —SO$_2$R$^{53a}$, —SR$^{53}$, —S(=O)R$^{53a}$, —SO$_2$N(R$^{53}$)$_2$, —N(R$^{53}$)$_2$, —NHC(=NH)NHR$^{53}$, —C(=NH)NHR$^{53}$, =NOR$^{53}$, NO$_2$, —C(=O)NHOR$^{53}$, —C(=O)NHNR$^{53}$R$^{53a}$, —OCH$_2$CO$_2$H, 2-(1-morpholino)ethoxy;
R$^{53}$, R$^{53a}$, and R$^{54}$ are each independently selected at each occurrence from the group: hydrogen, C$_1$–C$_6$ alkyl, and a bond to L$_n$;

$R^{80}$ and $R^{81}$ are independently selected from the group:

H, $C_1$–$C_{10}$ alkyl, —CN, —$CO_2R^{85}$, —C(=O) $R^{85}$, —C(=O)N($R^{85}$)$_2$, $C_2$–$C_{10}$ 1-alkene substituted with 0–3 $R^{84}$, $C_2$–$C_{10}$ 1-alkyne substituted with 0–3 $R^{84}$, aryl substituted with 0–3 $R^{84}$, unsaturated heterocycle substituted with 0–3 $R^{84}$, and unsaturated carbocycle substituted with 0–3 $R^{84}$, provided that when one of $R^{80}$ and $R^{81}$ is H or alkyl, then the other is not H or alkyl;

or, alternatively, $R^{80}$ and $R^{81}$, may be taken together with the shown divalent carbon radical to form:

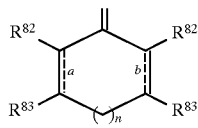

wherein:
$R^{82}$ and $R^{83}$ may be independently selected from the group: H, $R^{84}$, $C_1$–$C_{10}$ alkyl substituted with 0–3 $R^{84}$, $C_2$–$C_{10}$ alkenyl substituted with 0–3 $R^{84}$, $C_2$–$C_{10}$ alkynyl substituted with 0–3 $R^{84}$, aryl substituted with 0–3 $R^{84}$, heterocycle substituted with 0–3 $R^{84}$ and carbocycle substituted with 0–3 $R^{84}$;

or, alternatively, $R^{82}$, $R^{83}$ may be taken together to form a fused aromatic or heterocyclic ring;
$R^{84}$ is independently selected at each occurrence from the group: =O, F, Cl, Br, I, —$CF_3$, —CN, —$CO_2R^{85}$, —C(=O)$R^{85}$, —C(=O)N($R^{85}$)$_2$, —N($R^{85}$)$_3$+, —$CH_2OR^{85}$, —OC(=O)$R^{85}$, —OC(=O)O$R^{85a}$, —O$R^{85}$, —OC(=O)N($R^{85}$)$_2$, —$NR^{85}$C(=O)$R^{85}$, —$NR^{86}$C(=O)O$R^{85a}$, —$NR^{85}$C(=O)N($R^{85}$)$_2$, —$NR^{86}SO_2N$ ($R^{85}$)$_2$, —$NR^{86}SO_2R^{85a}$, —$SO_3H$, —$SO_2R^{85a}$, —$SR^{85}$, —S(=O)$R^{85a}$, —$SO_2N(R^{85})_2$, —N($R^{85}$)$_2$, —NHC(=NH) NH$R^{85}$, —C(=NH)NH$R^{85}$, =NO$R^{85}$, —C(=O)NHO$R^{85}$, —$OCH_2CO_2H$, 2-(1-morpholino) ethoxy; and
$R^{85}$, $R^{85a}$, and $R^{86}$ are each independently selected at each occurrence from the group: hydrogen and $C_1$–$C_6$ alkyl.

$X^1$ is independently selected at each occurrence from the group: $CR^{64}$ and N;
$X^2$ is independently selected at each occurrence from the group: $CR^{64}$, $CR^{64}R^{64}$, N, $NR^{64}$, O and S;
$X^3$ is independently selected at each occurrence from the group: C, $CR^{64}$, and N;
Y is selected from the group: $BR^{64-}$, $CR^{64}$, (P=O), (P=S);
provided the total number of heteroatoms in each ring of the heterocycle is 1 to 4;
$R^{64}$ is independently selected at each occurrence from the group:

H, $C_1$–$C_{10}$ alkyl substituted with 0–3 $R^{65}$, $C_2$–$C_{10}$ alkenyl substituted with 0–3 $R^{65}$, $C_2$–$C_{10}$ alkynyl substituted with 0–3 $R^{65}$, aryl substituted with 0–3 $R^{65}$, carbocycle substituted with 0–3 $R^{65}$ and $R^{65}$;

or, alternatively, two $R^{64}$ may be taken together with the atom or atoms to which they are attached to form a fused aromatic, carbocyclic or heterocyclic ring, substituted with 0–3 $R^{65}$;
$R^{65}$ is independently selected at each occurrence from the group: =O, F, Cl, Br, I, —$CF_3$, —CN, —$NO_2$, —$C_2R^{66}$, —C(=O)$R^{66}$, —C(=O)N ($R^{66}$)$_2$, —N($R^{66}$)$_3$+ —$CH_2OR^{66}$, —OC(=O)$R^{66}$, —OC(=O)O$R^{66a}$, —O$R^{66}$, —OC(=O)N($R^{66}$)$_2$, —$NR^{66}$C(=O)$R^{66}$, —$NR^{67}$C(=O)O$R^{66a}$, —$NR^{66}$C(=O)N($R^{66}$)$_2$, —$NR^{67}SO_2N(R^{66})_2$, —$NR^{67}SO_2R^{66a}$, —$SO_3H$, —$SO_2R^{66a}$, —$SO_2N$ ($R^{66}$)$_2$, —N($R^{66}$)$_2$, —$OCH_2CO_2H$; and
$R^{66}$, $R^{66a}$, and $R^{67}$ are each independently selected at each occurrence from the group: hydrogen and $C_1$–$C_6$ alkyl.

n is 0 or 1;
and a, b, c, d, e and f indicate the positions of optional double bonds, provided that one of e and f.

[12] Preferred kits of this invention are those wherein:
$A_{L1}$ is a functionalized aminocarboxylate;
Q is a biologically active molecule selected from the group: IIb/IIIa receptor antagonists, IIb/IIIa receptor ligands, fibrin binding peptides, leukocyte binding peptides, chemotactic peptides, somatostatin analogs, and selectin binding peptides;
d' is 1 to 3;
$L_n$ is:

wherein:
g" is 0–5;
f is 0–5;
f' is 1–5;
$Y^1$ and $Y^2$, at each occurrence, are independently selected from:
O, $NR^{56}$, C=O, C(=O)O, OC(=O)O, C(=O)NH, C=$NR^{56}$, S, SO, $SO_2$, $SO_3$, NHC(=O), (NH)$_2$C (=O), (NH)$_2$C=S;
$R^{55}$ and $R^{56}$ are independently selected at each occurrence from:
hydrogen; $C_1$–$C_{10}$ alkyl and alkaryl;
$R^{40}$ is independently selected at each occurrence from the group: aryl substituted with 0–3 $R^{52}$, and heterocycle substituted with 0–3 $R^{52}$;
$R^{41}$ is independently selected from the group: hydrogen, aryl substituted with 0–1 $R^{52}$, $C_1$–$C_3$ alkyl substituted with 0–1 $R^{52}$, and a heterocycle substituted with 0–1 $R^{52}$;
$R^{52}$ is independently selected at each occurrence from the group: a bond to $L_n$, —$CO_2R^{53}$, —$CH_2OR^{53}$, —$SO_3H$, —$SO_2R^{53a}$, —N($R^{53}$)$_2$, —N($R^{53}$)$_3$+, —NHC(=NH)NH$R^{53}$, and —$OCH_2CO_2H$;
$R^{53}$ and $R^{53a}$ are each independently selected at each occurrence from the group: hydrogen and $C_1$–$C_3$ alkyl;
$R^{80}$ is independently selected at each occurrence from the group: —$CO_2R^{85}$, $C_2$–$C_5$ 1-alkene substituted with 0–3 $R^{84}$, $C_2$–$C_5$ 1-alkyne substituted with 0–3 $R^{84}$, aryl substituted with 0–3 $R^{84}$, and unsaturated heterocycle substituted with 0–3 $R^{84}$;
$R^{81}$ is independently selected at each occurrence from the group: H and $C_1$–$C_5$ alkyl;
or, alternatively, $R^{80}$ and $R^{81}$, may be taken together with the shown divalent carbon radical to form:

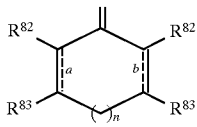

wherein:
$R^{82}$ and $R^{83}$ may be independently selected from the group: H and $R^{84}$;
or, alternatively, $R^{82}$, $R^{83}$ may be taken together to form a fused aromatic or heterocyclic ring;
  $R^{84}$ is independently selected at each occurrence from the group: $-CO_2R^{85}$, $-C(=O)N(R^{85})_2$, $-CH_2OR^{85}$, $-OC(=O)R^{85}$, $-OR^{85}$, $-SO_3H$, $-N(R^{85})_2$, and $-OCH_2CO_2H$;
    $R^{85}$ is independently selected at each occurrence from the group: hydrogen and $C_1-C_3$ alkyl.
Y is $BR^{64-}$;
$R^{64}$ is independently selected at each occurrence from the group: H, $C_1-C_3$ alkyl substituted with 0–3 $R^{65}$, aryl substituted with 0–3 $R^{65}$ and $R^{65}$;
or, alternatively, two $R^{64}$ may be taken together with the atom or atoms to which they are attached to form a fused aromatic, or heterocyclic ring, substituted with 0–3 $R^{65}$;
  $R^{65}$ is independently selected at each occurrence from the group: $-NO_2$, $-CO_2R^{66}$, $-OR^{66}$, $-SO_3H$, and $-OCH_2CO_2H$;
    $R^{66}$ is hydrogen; and
n is 0.

[13] Also preferred are those kits wherein:
$A_{L1}$ is a tricine;
Q is a biologically active molecule selected from the group: IIb/IIIa receptor antagonists, and chemotactic peptides;
d' is 1;
$Y^1$ and $Y^2$, at each occurrence, are independently selected from:
  O, $NR^{56}$, C=O, C(=O)O, OC(=O)O, C(=O)NH, C=$NR^{56}$, NHC(=O), $(NH)_2C(=O)$;
$R^{55}$ and $R^{56}$ are hydrogen;
$R^{40}$ is heterocycle substituted with $R^{52}$;
$R^{41}$ is hydrogen;
$R^{52}$ is a bond to $L_n$;
$R^{80}$ is independently selected at each occurrence from the group: $-CO_2R^{85}$, $C_2-C_3$ 1-alkene substituted with 0–1 $R^{84}$, aryl substituted with 0–1 $R^{84}$, and unsaturated heterocycle substituted with 0–1 $R^{84}$;
$R^{81}$ is H;
$R^{84}$ is independently selected at each occurrence from the group: $-CO_2R^{85}$, $-OR^{85}$, $-SO_3H$, and $-N(R^{85})_2$;
$R^{85}$ is independently selected at each occurrence from the group: hydrogen and methyl;
$X^1$ is independently selected at each occurrence from the group: $CR^{64}$ and N;
$X^2$ is independently selected at each occurrence from the group: $CR^{64}$, $CR^{64}R^{64}$, N, $NR^{64}$, and O;
$X^3$ is N;
Y is $BR^{64-}$;
provided the total number of heteroatoms in each ring of the ligand $A_{L2}$ is 2 to 3;
$R^{64}$ is independently selected at each occurrence from the group:
  H, $C_1-C_3$ alkyl substituted with 0–1 $R^{65}$, aryl substituted with 0–1 $R^{65}$, and $R^{65}$;

$R^{65}$ is independently selected at each occurrence from the group: $-NO_2$, $-CO_2R^{66}$, $-OR^{66}$, and $-SO_3H$;
$R^{66}$ is hydrogen;
n is 0;
and a, b, c, d, e and f indicate the positions of optional double bonds, provided that one of e and f is a double bond.

[14] Also preferred are those kits wherein:
$A_{L2}$ is selected from the group:

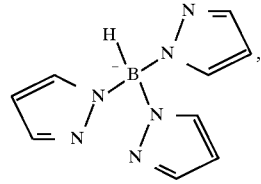

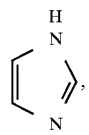

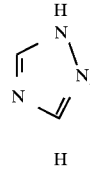

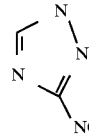

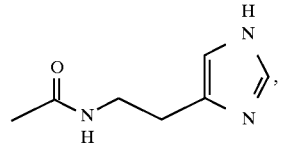

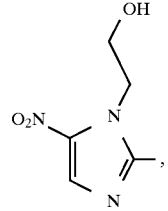

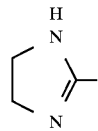

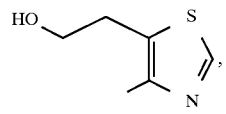

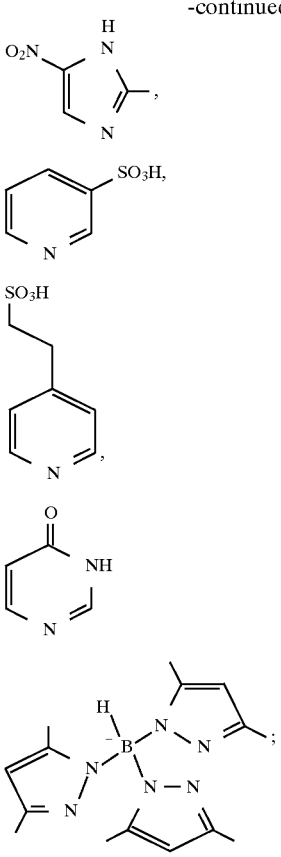

Q is

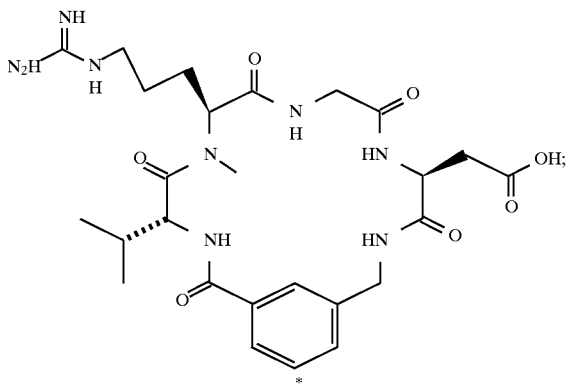

d' is 1;
L$_n$ is attached to Q at the carbon atom designated with a * and has the formula:

—(C=O)NH(CH$_2$)$_5$C(=O)NH—;

C$_h$ is selected from R$^{40}$NNH$_2$— and R$^{40}$R$^{41}$N—N=CR$^{80}$R$^{81}$, wherein, R$^{40}$ is independently selected at each occurrence from the group: heterocycle substituted with R$^{52}$;

R$^{41}$ is hydrogen;

R$^{52}$ is a bond to L$_n$;

R$^{80}$ is independently selected at each occurrence from the group: —CO$_2$R$^{85,}$ C$_2$–C$_3$ 1-alkene substituted with 0–1 R$^{84,}$ aryl substituted with 0–1 R$^{84}$ and unsaturated heterocycle substituted with 0–1 R$^{84}$;

R$^{81}$ is H;

R$^{84}$ is independently selected at each occurrence from the group: —CO$_2$R$^{85}$, —OR$^{85}$, —SO$_3$H, and —N(R$^{85}$)$_2$;

R$^{85}$ is independently selected at each occurrence from the group: hydrogen and methyl.

When any variable occurs more than one time in any constituent or in any formula, its definition on each occurrence is independent of its definition at every other occurrence. Thus, for example, if a group is shown to be substituted with 0–2 R$^{52}$, then said group may optionally be substituted with up to two R$^{52}$ and R$^{52}$ at each occurrence is selected independently from the defined list of possible R$^{52}$. Also, by way of example, for the group —N(R$^{53}$)$_2$, each of the two R$^{53}$ substituents on N is independently selected from the defined list of possible R$^{53}$. Combinations of substituents and/or variables are permissible only if such combinations result in stable compounds.

By "stable compound" or "stable structure" is meant herein a compound that is sufficiently robust to survive isolation to a useful degree of purity from a reaction mixture, and formulation into an efficacious diagnostic agent.

The term "capable of stabilizing", as used herein to describe the second ancillary ligand A$_{L2}$, means that the ligand is capable of coordinating to the transition metal radionuclide in the presence of the first ancillary ligand and the transition metal chelator, under the conditions specified herein, resulting in a radiopharmaceutical of Formula 1 having a minimal number of isomeric forms, the relative ratios of which do not change significantly with time, and that remains substantially intact upon dilution.

The term "substituted", as used herein, means that one or more hydrogens on the designated atom or group is replaced with a selection from the indicated group, provided that the designated atom's or group's normal valency is not exceeded, and that the substitution results in a stable compound. When a substituent is keto (i.e., =O), then 2 hydrogens on the atom are replaced.

The term "bond", as used herein, means either a single or double bond.

The term "salt", as used herein, is used as defined in the *CRC Handbook of Chemistry and Physics*, 65th Edition, CRC Press, Boca Raton, Fla., 1984, as any substance which yields ions, other than hydrogen or hydroxyl ions.

As used herein, "alkyl" is intended to include both branched and straight-chain saturated aliphatic hydrocarbon groups having the specified number of carbon atoms; "cycloalkyl" or "mcarbocycle" is intended to include saturated and partially unsaturated ring groups, including mono-, bi- or poly-cyclic ring systems, such as cyclopropyl, cyclobutyl, cyclopentyl, cyclohexyl, cycloheptyl, cyclooctyl and adamantyl; "bicycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth.

As used herein, the term "alkene" or "alkenyl" is intended to include both branched and straight-chain groups of the formula C$_n$H$_{2n-1}$ having the specified number of carbon atoms.

As used herein, the term "alkyne" or "alkynyl" is intended to include both branched and straight-chain groups of the formula C$_n$H$_{2n-3}$ having the specified number of carbon atoms.

As used herein, "aryl" or "aromatic residue" is intended to mean phenyl or naphthyl, which when substituted, the substitution can be at any position.

As used herein, the term "heterocycle" or "heterocyclic ring system" is intended to mean a stable 5- to 7-membered monocyclic or bicyclic or 7- to 10-membered bicyclic heterocyclic ring which may be saturated, partially unsaturated, or aromatic, and which consists of carbon atoms and from 1 to 4 heteroatoms selected independently from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, benzopyranyl, thiadiazine, tetrazolyl, benzofuranyl, benzothiophenyl, indolene, quinoline, isoquinolinyl or benzimidazolyl, piperidinyl, 4-piperidone, 2-pyrrolidone, tetrahydrofuran, tetrahydroquinoline, tetrahydroisoquinoline, decahydroquinoline, octahydroisoquinoline, azocine, triazine (including 1,2,3-, 1,2,4-, and 1,3,5-triazine), 6H-1,2,5-thiadiazine, 2H, 6H-1,5,2-dithiazine, thiophene, tetrahydrothiophene, thianthrene, furan, pyran, isobenzofuran, chromene, xanthene, phenoxathiin, 2H-pyrrole, pyrrole, imidazole, pyrazole, thiazole, isothiazole, oxazole (including 1,2,4- and 1,3,4-oxazole), isoxazole, triazole, pyridine, pyrazine, pyrimidine, pyridazine, indolizine, isoindole, 3H-indole, indole, 1H-indazole, purine, 4H-quinolizine, isoquinoline, quinoline, phthalazine, naphthyridine, quinoxaline, quinazoline, cinnoline, pteridine, 4aH-carbazole, carbazole, β-carboline, phenanthridine, acridine, perimidine, phenanthroline, phenazine, phenarsazine, phenothiazine, furazan, phenoxazine, isochroman, chroman, pyrrolidine, pyrroline, imidazolidine, imidazoline, pyrazolidine, pyrazoline, piperazine, indoline, isoindoline, quinuclidine, or morpholine. Also included are fused ring and spiro compounds containing, for example, the above heterocycles.

As used herein, the term "alkaryl" means an aryl group bearing an alkyl group of 1–10 carbon atoms; the term "aralkyl" means an alkyl group of 1–10 carbon atoms bearing an aryl group; the term "arylalkaryl" means an aryl group bearing an alkyl group of 1–10 carbon atoms bearing an aryl group; and the term "heterocycloalkyl" means an alkyl group of 1–10 carbon atoms bearing a heterocycle.

A "reducing agent" is a compound that reacts with the radionuclide, which is typically obtained as a relatively unreactive, high oxidation state compound, to lower its oxidation state by transfering electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

A "transfer ligand" is a ligand that forms an intermediate complex with the radionuclide that is stable enough to prevent unwanted side-reactions but labile enough to be converted to the radiopharmaceutical. The formation of the intermediate complex is kinetically favored while the formation of the radiopharmaceutical is thermodynamically favored. Transfer ligands useful in the preparation of radiopharmaceuticals and in diagnostic kits useful for the preparation of said radiopharmaceuticals include but are not limited to gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor atoms.

The term "donor atom" refers to the atom directly attached to a metal by a chemical bond.

"Ancillary" or "co-ligands" are ligands that are incorporated into the radiopharmaceutical during its synthesis. They serve to complete the coordination sphere of the radionuclide together with the chelator or radionuclide bonding unit of the reagent. For radiopharmaceuticals comprised of a binary ligand system, the radionuclide coordination sphere is composed of one or more chelators or bonding units from one or more reagents and one or more ancillary or co-ligands, provided that there are a total of two types of ligands, chelators or bonding units. For example, a radiopharmaceutical comprised of one chelator or bonding unit from one reagent and two of the same ancillary or co-ligands and a radiopharmaceutical comprised of two chelators or bonding units from one or two reagents and one ancillary or co-ligand are both considered to be comprised of binary ligand systems. For radiopharmaceuticals comprised of a ternary ligand system, the radionuclide coordination sphere is composed of one or more chelators or bonding units from one or more reagents and one or more of two different types of ancillary or co-ligands, provided that there are a total of three types of ligands, chelators or bonding units. For example, a radiopharmaceutical comprised of one chelator or bonding unit from one reagent and two different ancillary or co-ligands is considered to be comprised of a ternary ligand system.

Ancillary or co-ligands useful in the preparation of radiopharmaceuticals and in diagnostic kits useful for the preparation of said radiopharmaceuticals are comprised of one or more oxygen, nitrogen, carbon, sulfur, phosphorus, arsenic, selenium, and tellurium donor atoms. A ligand can be a transfer ligand in the synthesis of a radiopharmaceutical and also serve as an ancillary or co-ligand in another radiopharmaceutical. Whether a ligand is termed a transfer or ancillary or co-ligand depends on whether the ligand remains in the radionuclide coordination sphere in the radiopharmaceutical, which is determined by the coordination chemistry of the radionuclide and the chelator or bonding unit of the reagent or reagents.

A "chelator" or "bonding unit" is the moiety or group on a reagent that binds to a metal radionuclide through the formation of chemical bonds with one or more donor atoms.

The term "binding site" means the site in vivo or in vitro that binds a biologically active molecule.

A "diagnostic kit" comprises a collection of components, termed the formulation, in one or more vials which are used by the practising end user in a clinical or pharmacy setting to synthesize the radiopharmaceutical. The kit provides all the requisite components to synthesize and use the radiopharmaceutical except those that are commonly available to the practising end user, such as water or saline for injection, a solution of the radionuclide, equipment for heating the kit during the synthesis of the radiopharmaceutical if required, equipment necessary for administering the radiopharmaceutical to the patient such as syringes and shielding, and imaging equipment.

A "buffer" is a compound that is used to control the pH of the kit during its manufacture and during the synthesis of the radiopharmaceutical.

A "lyophilization aid" is a component that has favorable physical properties for lyophilization, such as the glass transition temperature, and is added to the diagnostic kit to improve the physical properties of the combination of all the components of the kit for lyophilization.

A "stabilization aid" is a component that is added to the radiopharmaceutical or to the diagnostic kit either to stabilize the radiopharmaceutical once it is synthesized or to prolong the shelf-life of the kit before it must be used. Stabilization aids can be antioxidants, reducing agents or radical scavengers and can provide improved stability by reacting preferentially with species that degrade other components or the radiopharmaceutical.

A "solubilization aid" is a component that improves the solubility of one or more other components in the medium required for the synthesis of the radiopharmaceutical.

A "bacteriostat" is a component that inhibits the growth of bacteria in the diagnostic kit either during its storage before use of after the kit is used to synthesize the radiopharmaceutical.

The radiopharmaceuticals of the present invention are of the formula $[(Q)_{d'}L_n\text{—}C_{h'}]_x\text{—}M_t(A_{L1})_y(A_{L2})_z$, wherein Q is a biologically active group, d' is an integer from 1 to 20, $L_n$ is an optional linking group, $C_{h'}$ is a radionuclide metal chelator or bonding unit bound to the transition metal radionuclide, $M_t$, of the formulae $R^{40}N\!=\!N^+\!=$, $R^{40}R^{41}N\text{—}N\!=$, or $R^{40}N\!=\!N(H)\text{—}$, $A_{L1}$ is a first ancillary or co-ligand, $A_{L2}$ is a second ancillary or co-ligand, x, y and z are independently 1 or 2.

The biologically active molecule Q can be a protein, antibody, antibody fragment, peptide or polypeptide, or peptidomimetic that is comprised of a recognition sequence or unit for a receptor or binding site expressed at the site of the disease, or for a receptor or binding site expressed on platelets or leukocytes. The exact chemical composition of Q is selected based on the disease state to be diagnosed, the mechanism of localization to be utilized, and to provide an optimum combination of rates of localization, clearance and radionuclidic decay.

For the purposes of this invention, the term thromboembolic disease is taken to include both venous and arterial disorders and pulmonary embolism, resulting from the formation of blood clots.

For the diagnosis of thromboembolic disorders or atherosclerosis, Q is selected from the group including the cyclic IIb/IIIa receptor antagonist compounds described in co-pending U.S. Ser. No. 08/218,861 (equivalent to WO 94/22494); the RGD containing peptides described in U.S. Pat. Nos. 4,578,079, 4,792,525, the applications PCT US88/04403, PCT US89/01742, PCT US90/03788, PCT US91/02356 and by Ojima et. al., 204th Meeting of the Amer. Chem. Soc., 1992, Abstract 44; the peptides that are fibrinogen receptor antagonists described in European Patent Applications 90202015.5, 90202030.4, 90202032.2, 90202032.0, 90311148.2, 90311151.6, 90311537.6, the specific binding peptides and polypeptides described as IIb/IIIa receptor ligands, ligands for the polymerization site of fibrin, laminin derivatives, ligands for fibrinogen, or thrombin ligands in PCT WO 93/23085 (excluding the technetium binding groups); the oligopeptides that correspond to the IIIa protein described in PCT WO90/00178; the hirudin-based peptides described in PCT WO90/03391; the IIb/IIIa receptor ligands described in PCT WO90/15818; the thrombus, platelet binding or atherosclerotic plaque binding peptides described in PCT WO92/13572 (excluding the technetium binding group) or GB 9313965.7; the fibrin binding peptides described in U.S. Pat. Nos. 4,427,646 and 5,270,030; the hirudin-based peptides described in U.S. Pat. No. 5,279,812; or the fibrin binding proteins described in U.S. Pat. No. 5,217,705; the guanine derivatives that bind to the IIb/IIIa receptor described in U.S. Pat. No. 5,086,069; or the tyrosine derivatives described in European Patent Application 0478328A1, and by Hartman et. al., J. Med. Chem., 1992, 35, 4640; or oxidized low density lipoprotein (LDL).

For the diagnosis of infection, inflammation or transplant rejection, Q is selected from the group including the leukocyte binding peptides described in PCT WO93/17719 (excluding the technetium binding group), PCT WO92/13572 (excluding the technetium binding group) or U.S. Ser. No. 08/140000; the chemotactic peptides described in Eur. Pat. Appl. 90108734.6 or A. Fischman et. al., Semin. Nuc. Med., 1994, 24, 154; or the leukostimulatory agents described in U.S. Pat. No. 5,277,892.

For the diagnosis of cancer, Q is selected from the group of somatostatin analogs described in UK Application 8927255.3 or PCT WO94/00489, the selectin binding peptides described in PCT WO94/05269, the biological-function domains described in PCT WO93/12819, Platelet Factor 4 or the growth factors (PDGF, EGF, FGF, TNF, MCSF or Il-8).

Q may also represent proteins, antibodies, antibody fragments, peptides, polypeptides, or peptidomimetics that bind to receptors or binding sites on other tissues, organs, enzymes or fluids. Examples include the β-amyloid proteins that have been demonstrated to accumulate in patients with Alzheimer's disease, atrial naturetic factor derived peptides that bind to myocardial and renal receptors, antimyosin antibodies that bind to areas of infarcted tissues, or nitroimidazole derivatives that localize in hypoxia areas in vivo.

The group $C_{h'}$ is termed a hydrazido (of formula $R^{40}R^{41}N\text{—}N\!=$), or diazenido (of formula $R^{40}N\!=\!N^+\!=$ or $R^{40}N\!=\!N(H)\text{—}$) group and serves as the point of attachment of the radionuclide to the remainder of the radiopharmaceutical designated by the formula $(Q)_{d'}\text{—}L_n$ or $(Q)_{d'}$. A diazenido group can be either terminal (only one atom of the group is bound to the radionuclide) or chelating. In order to have a chelating diazenido group at least one other atom of the group, located on $R^{40}$, must also be bound to the radionuclide. The atoms bound to the metal are termed donor atoms.

The transition metal radionuclide, $M_t$, is selected from the group: technetium-99m, rhenium-186 and rhenium-188. For diagnostic purposes Tc-99m is the preferred isotope. Its 6 hour half-life and 140 keV gamma ray emission energy are almost ideal for gamma scintigraphy using equipment and procedures well established for those skilled in the art. The rhenium isotopes also have gamma ray emission energies that are compatible with gamma scintigraphy, however, they also emit high energy beta particles that are more damaging to living tissues. These beta particle emissions can be utilized for therapeutic purposes, for example, cancer radiotherapy.

The coordination sphere of the radionuclide includes all the ligands or groups bound to the radionuclide. For a transition metal radionuclide, $M_t$, to be stable it typically has a coordination number (number of donor atoms) comprised of an integer greater than or equal to 4 and less than or equal to 8; that is there are 4 to 8 atoms bound to the metal and it is said to have a complete coordination sphere. The requisite coordination number for a stable radionuclide complex is determined by the identity of the radionuclide, its oxidation state, and the type of donor atoms. If the chelator or bonding unit $C_{h'}$ does not provide all of the atoms necessary to stabilize the metal radionuclide by completing its coordination sphere, the coordination sphere is completed by donor atoms from other ligands, termed ancillary or co-ligands, which can also be either terminal or chelating.

A large number of ligands can serve as ancillary or co-ligands, the choice of which is determined by a variety of considerations such as the ease of synthesis of the radiopharmaceutical, the chemical and physical properties of the ancillary ligand, the rate of formation, the yield, and the number of isomeric forms of the resulting radiopharmaceuticals, the ability to administer said ancillary or co-ligand to a patient without adverse physiological consequences to said patient, and the compatibility of the ligand in a lyophilized kit formulation. The charge and lipophilicity of the ancillary ligand will effect the charge and lipophilicity of the radiopharmaceuticals. For example, the use of 4,5-dihydroxy-1,3-benzene disulfonate results in radiopharmaceuticals with an additional two anionic groups because the sulfonate groups will be anionic under physiological conditions. The use of N-alkyl substituted 3,4-hydroxypyridinones results in radiopharmaceuticals with varying degrees of lipophilicity depending on the size of the alkyl substituents.

The radiopharmaceuticals of the present invention are comprised of two types of ancillary or co-ligands designated $A_{L1}$ and $A_{L2}$. Ancillary ligands $A_{L1}$ are comprised of two or more hard donor atoms such as oxygen and amine nitrogen (sp$^3$ hydribidized). The donor atoms occupy at least two of the sites in the coordination sphere of the radionuclide metal, $M_r$; the ancillary ligand $A_{L1}$ serves as one of the three ligands in the ternary ligand system. Examples of ancillary ligands $A_{L1}$ include but are not limited to dioxygen ligands and functionalized aminocarboxylates. A large number of such ligands are available from commercial sources.

Ancillary dioxygen ligands include ligands that coordinate to the metal ion through at least two oxygen donor atoms. Examples include but are not limited to: glucoheptonate, gluconate, 2-hydroxyisobutyrate, lactate, tartrate, mannitol, glucarate, maltol, Kojic acid, 2,2-bis (hydroxymethyl)propionic acid, 4,5-dihydroxy-1,3-benzene disulfonate, or substituted or unsubstituted 1,2 or 3,4 hydroxypyridinones. (The names for the ligands in these examples refer to either the protonated or non-protonated forms of the ligands.)

Functionalized aminocarboxylates include ligands that have a combination of amine nitrogen and oxygen donor atoms. Examples include but are not limited to: iminodiacetic acid, 2,3-diaminopropionic acid, nitrilotriacetic acid, N,N'-ethylenediamine diacetic acid, N,N,N'-ethylenediamine triacetic acid, hydroxyethylethylenediamine triacetic acid, and N,N'-ethylenediamine bis-hydroxyphenylglycine. (The names for the ligands in these examples refer to either the protonated or non-protonated forms of the ligands.)

A series of functionalized aminocarboxylates are disclosed by Bridger et. al. in U.S. Pat. No. 5,350,837, herein incorporated by reference, that result in improved rates of formation of technetium labeled hydrazino modified proteins. We have determined that certain of these aminocarboxylates result in improved yields of the radiopharmaceuticals of the present invention. The preferred ancillary ligands $A_{L1}$ functionalized aminocarboxylates that are derivatives of glycine; the most preferred is tricine (tris (hydroxymethyl)methylglycine).

The second type of ancillary ligands $A_{L2}$ are comprised of one or more soft donor atoms selected from the group: imine nitrogen (sp$^2$ hydribidized), sulfur (sp$^2$ hydribidized) and carbon (sp hybridized); atoms which have π-acid character. Ligands $A_{L2}$ can be monodentate, bidentate or tridentate, the denticity is defined by the number of donor atoms in the ligand. One of the two donor atoms in a bidentate ligand and one of the three donor atoms in a tridentate ligand must be a soft donor atom.

The ligands $A_{L2}$ that are comprised of imine nitrogen are unsaturated or aromatic nitrogen-containing, 5 or 6-membered heterocycles. The ligands that are comprised of sulfur (sp$^2$ hybridized) donor atoms are thiocarbonyls, comprised of the moiety C=S. The ligands comprised of carbon (sp hybridized) donor atoms are isonitriles, comprised of the moiety CNR, where R is an organic radical. A large number of such ligands are available from commercial sources. Isonitriles can be synthesized as described in European Patent 0107734 and in U.S. Pat. No. 5,279,811, herein incorporated by reference. Preferred ancillary ligands $A_{L2}$ are unsaturated or aromatic 5 or 6 membered heterocycles. The most preferred ancillary ligands $A_{L2}$ are unsaturated 5 membered heterocycles.

The ancillary ligands $A_{L2}$ may be substituted with alkyl, aryl, alkoxy, heterocycle, aralkyl, alkaryl and arylalkaryl groups and may or may not bear functional groups comprised of heteroatoms such as oxygen, nitrogen, phosphorus or sulfur. Examples of such functional groups include but are not limited to: hydroxyl, carboxyl, carboxamide, nitro, ether, ketone, amino, ammonium, sulfonate, sulfonamide, phosphonate, and phosphonamide. The functional groups may be chosen to alter the lipophilicity and water solubility of the ligands which may affect the biological properties of the radiopharmaceuticals, such as altering the distribution into non-target tissues, cells or fluids, and the mechanism and rate of elimination from the body.

The radiopharmaceuticals of the present invention can be easily prepared by admixing a salt of a radionuclide, a reagent of Formula 2, an ancillary ligand $A_{L1}$, an ancillary ligand $A_{L2}$, and a reducing agent, in an aqueous solution at temperatures from room temperature to 100° C.

$$(Q)_{d'}L_n\text{—}C_h \qquad (2)$$

and pharmaceutically acceptable salts thereof, wherein: Q, d', $L_n$ are as defined above, $C_h$ is a radionuclide metal chelator selected from the group: $R^{40}R^{41}N\text{—}N\text{=}C(C_1\text{-}C_3$ alkyl)$_2$ and $R^{40}NNH_2\text{—}$, and $R^{40}R^{41}N\text{—}N\text{=}C(R^{80})(R^{81})$, and pharmaceutically acceptable salts thereof. The synthesis of reagents of formula 2 is described in co-pending U.S. Ser. No. 08/218,861 (equivalent to WO 94/22494) and in co-pending U.S. Ser. No. 08/476,296.

When $C_h$ is a hydrazone group, then it must first be converted to a hydrazine of formula $R^{40}R^{41}NNH_2$, which may or may not be protonated, prior to complexation with the metal radionuclide, $M_r$. The chelator or bonding unit, $C_h$, when bound to the metal radionuclide, $M_r$, is designated $C_{h'}$. The conversion of the hydrazone group to the hydrazine can occur either prior to reaction with the radionuclide, in which case the radionuclide and the ancillary or co-ligand or ligands are combined not with the reagent but with a hydrolyzed form of the reagent bearing the chelator or bonding unit, $C_h$, or in the presence of the radionuclide in which case the reagent itself is combined with the radionuclide and the ancillary or co-ligand or ligands. In the latter case, the pH of the reaction mixture must be neutral or acidic.

Alternatively, the radiopharmaceuticals of the present invention can be prepared by first admixing a salt of a radionuclide, an ancillary ligand $A_{L1}$, and a reducing agent in an aqueous solution at temperatures from room temperature to 100° C. to form an intermediate radionuclide complex with the ancillary ligand $A_{L1}$ then adding a reagent of Formula 2 and an ancillary ligand $A_{L2}$ and reacting further at temperatures from room temperature to 100° C.

Alternatively, the radiopharmaceuticals of the present invention can be prepared by first admixing a salt of a radionuclide, an ancillary ligand $A_{L1}$, a reagent of Formula 2, and a reducing agent in an aqueous solution at temperatures from room temperature to 100° C. to form an intermediate radionuclide complex, and then adding an ancillary ligand $A_{L2}$ and reacting further at temperatures from room temperature to 100° C.

The total time of preparation will vary depending on the identity of the radionuclide, the identities and amounts of the reactants and the procedure used for the preparation. The preparations may be complete, resulting in >80% yield of the radiopharmaceutical, in 1 minute or may require more time. If higher purity radiopharmaceuticals are needed or desired, the products can be purified by any of a number of techniques well known to those skilled in the art such as liquid chromatography, solid phase extraction, solvent extraction, dialysis or ultrafiltration.

The technetium and rhenium radionuclides are preferably in the chemical form of pertechnetate or perrhenate and a pharmaceutically acceptable cation. The pertechnetate salt form is preferably sodium pertechnetate such as obtained from commercial Tc-99m generators. The amount of pertechnetate used to prepare the radiopharmaceuticals of the present invention can range from 0.1 mCi to 1 Ci, or more preferably from 1 to 200 mCi.

The amount of the reagent of formula 2 used to prepare the radiopharmaceuticals of the present invention can range from 0.1 µg to 10 mg, or more preferably from 0.5 µg to 100 µg. The amount used will be dictated by the amounts of the other reactants and the identity of the radiopharmaceuticals of Formula 1 to be prepared.

The amounts of the ancillary ligands $A_{L1}$ used can range from 0.1 mg to 1 g, or more preferrably from 1 mg to 100 mg. The exact amount for a particular radiopharmaceutical is a function of identity of the radiopharmaceuticals of Formula 1 to be prepared, the procedure used and the amounts and identities of the other reactants. Too large an amount of $A_{L1}$ will result in the formation of by-products comprised of technetium labeled $A_{L1}$ without a biologically active molecule or by-products comprised of technetium labeled biologically active molecules with the ancillary ligand $A_{L1}$ but without the ancillary ligand $A_{L2}$. Too small an amount of $A_{L1}$ will result in other by-products such as technetium labeled biologically active molecules with the ancillary ligand $A_{L2}$ but without the ancillary ligand $A_{L1}$, or reduced hydrolyzed technetium, or technetium colloid.

The amounts of the ancillary ligands $A_{L2}$ used can range from 0.001 mg to 1 g, or more preferrably from 0.01 mg to 10 mg. The exact amount for a particular radiopharmaceutical is a function of the identity of the radiopharmaceuticals of Formula 1 to be prepared, the procedure used and the amounts and identities of the other reactants. Too large an amount of $A_{L2}$ will result in the formation of by-products comprised of technetium labeled $A_{L2}$ without a biologically active molecule or by-products comprised of technetium labeled biologically active molecules with the ancillary ligand $A_{L2}$ but without the ancillary ligand $A_{L1}$. If the moiety $(Q)_{d'}-L_n-C_{h'}$ bears one or more substituents that are comprised of a soft donor atom, as defined above, at least a ten-fold molar excess of the ancillary ligand $A_{L2}$ to the reagent of formula 2 is required to prevent the substituent from interfering with the coordination of the ancillary ligand $A_{L2}$ to the metal radionuclide, $M_r$.

Suitable reducing agents for the synthesis of the radiopharmaceuticals of the present invention include stannous salts, dithionite or bisulfite salts, borohydride salts, and formamidinesulfinic acid, wherein the salts are of any pharmaceutically acceptable form. The preferred reducing agent is a stannous salt. The amount of a reducing agent used can range from 0.001 mg to 10 mg, or more preferably from 0.005 mg to 1 mg.

The specific structure of a radiopharmaceutical of the present invention will depend on the identity of the biologically active molecule Q, the number d', the identity of the linker $L_n$, the identity of the chelator moiety $C_{h'}$, the identity of the ancillary ligand $A_{L1}$, the identity of the ancillary ligand $A_{L2}$, and the identity of the radionuclide $M_r$. The identities of Q, $L_n$, and $C_{h'}$ and the number d' are determined by the choice of the reagent of Formulae 2 or 3. For a given reagent of Formulae 2 or 3, the amount of the reagent, the amount and identity of the ancillary ligands $A_{L1}$ and $A_{L2}$, the identity of the radionuclide $M_t$ and the synthesis conditions employed will determine the structure of the radiopharmaceutical of Formula 1.

Radiopharmaceuticals synthesized using concentrations of reagents of Formulae 2 or 3 of <100 µg/mL, will be comprised of one hydrazido or diazenido group $C_{h'}$; the value of x will be 1. Those synthesized using >1 mg/mL concentrations will be comprised of two hydrazido or diazenido groups; the value of x will be 2. The two $C_{h'}$ groups may be the same or different. For most applications, only a limited amount of the biologically active molecule can be injected and not result in undesired side-effects, such as chemical toxicity, interference with a biological process or an altered biodistibution of the radiopharmaceutical. Therefore, the radiopharmaceuticals with x equal to 2, which require higher concentrations of the reagents of Formula 2 comprised in part of the biologically active molecule, will have to be diluted or purified after synthesis to avoid such side-effects.

The identities and amounts used of the ancillary ligands $A_{L1}$ and $A_{L2}$ will determine the values of the variables y and z. The values of y and z can independently be an integer from 1 to 2. In combination, the values of y and z will result in a technetium coordination sphere that is made up of at least five and no more than seven donor atoms. For monodentate ancillary ligands $A_{L2}$, z can be an integer from 1 to 2; for bidentate or tridentate ancillary ligands $A_{L2}$, z is 1. The preferred combination for monodentate ligands is y equal to 1 or 2 and z equal to 1. The preferred combination for bidentate or tridentate ligands is y equal to 1 and z equal to 1.

Another aspect of the present invention are diagnostic kits for the preparation of radiopharmaceuticals useful as imaging agents for the diagnosis of cardiovascular disorders, infectious disease, inflammatory disease and cancer. Diagnostic kits of the present invention comprise one or more vials containing the sterile, non-pyrogenic, formulation comprised of a predetermined amount of the reagent of formulae $(Q)_{d'}-L_n-C_h$ or $(Q)_{d'}-L_n-H_z$, one or two ancillary or co-ligands and optionally other components such as reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practising end user, the ease of manufacturing the kit, the shelf-life of the kit, or the stability and shelf-life of the radiopharmaceutical. The improvement achieved by the inclusion of an optional component in the formulation must be weighed against the added complexity of the formulation and added cost to manufacture the kit. The one or more vials that contain all or part of the formulation can independently be in the form of a sterile solution or a lyophilized solid.

Buffers useful in the preparation of radiopharmaceuticals and in diagnostic kits useful for the preparation of said radiopharmaceuticals include but are not limited to phosphate, citrate, sulfosalicylate, and acetate. A more complete list can be found in the United States Pharmacopeia.

Lyophilization aids useful in the preparation of diagnostic kits useful for the preparation of radiopharmaceuticals include but are not limited to mannitol, lactose, sorbitol, dextran, Ficoll, and polyvinylpyrrolidine(PVP).

Stabilization aids useful in the preparation of radiopharmaceuticals and in diagnostic kits useful for the preparation of said radiopharmaceuticals include but are not limited to ascorbic acid, cysteine, monothioglycerol, sodium bisulfite, sodium metabisulfite, gentisic acid, and inositol.

Solubilization aids useful in the preparation of radiopharmaceuticals and in diagnostic kits useful for the preparation of said radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly(oxyethylene) block copolymers (Pluronics) and lecithin. Preferred solubilizing aids are polyethylene glycol, and Pluronics.

Bacteriostats useful in the preparation of radiopharmaceuticals and in diagnostic kits useful for the preparation of said radiopharmaceuticals include but are not limited to benzyl alcohol, benzalkonium chloride, chlorbutanol, and methyl, propyl or butyl paraben.

A component in a diagnostic kit can also serve more than one function. A reducing agent can also serve as a stabilization aid, a buffer can also serve as a transfer ligand, a lyophilization aid can also serve as a transfer, ancillary or co-ligand and so forth.

The predetermined amounts of each component in the formulation are determined by a variety of considerations that are in some cases specific for that component and in other cases dependent on the amount of another component or the presence and amount of an optional component. In general, the minimal amount of each component is used that will give the desired effect of the formulation. The desired effect of the formulation is that the practising end user can synthesize the radiopharmaceutical and have a high degree of certainty that the radiopharmaceutical can be safely injected into a patient and will provide diagnostic information about the disease state of that patient.

The diagnostic kits of the present invention will also contain written instructions for the practising end user to follow to synthesize the radiopharmaceuticals. These instructions may be affixed to one or more of the vials or to the container in which the vial or vials are packaged for shipping or may be a separate insert, termed the package insert.

Another aspect of the present invention contemplates a method of imaging the site of thrombotic disease in a patient involving: (1) synthesizing a radiopharmaceutical using a reagent of the present invention capable of localizing at sites of thrombotic disease due to an interaction between the biologically active group, Q, of the radiopharmaceutical and a receptor or binding site expressed at the site of the disease or with a receptor or binding site on an endogenous blood component that accumulates at the site; (2) administering said radiopharmaceutical to a patient by injection or infusion; (3) imaging the patient using either planar or SPECT gamma scintigraphy.

Another aspect of the present invention contemplates a method of imaging the site of infection or infectious disease in a patient involving: (1) synthesizing a radiopharmaceutical using a reagent of the present invention capable of localizing at sites of infection or infectious disease due to an interaction between the biologically active group, Q, of the radiopharmaceutical and a receptor or binding site expressed at the site of the disease or with a receptor or binding site on an endogenous blood component that accumulates at the site; (2) administering said radiopharmaceutical to a patient by injection or infusion; (3) imaging the patient using either planar or SPECT gamma scintigraphy.

Another aspect of the present invention contemplates a method of imaging the site of inflammation in a patient involving: (1) synthesizing a radiopharmaceutical using a reagent of the present invention capable of localizing at sites of inflammation due to an interaction between the biologically active group, Q, of the radiopharmaceutical and a receptor or binding site expressed at the site of inflammation or with a receptor or binding site on an endogenous blood component that accumulates at the site; (2) administering said radiopharmaceutical to a patient by injection or infusion; (3) imaging the patient using either planar or SPECT gamma scintigraphy.

Another aspect of the present invention contemplates a method of imaging the site of cancer in a patient involving: (1) synthesizing a radiopharmaceutical using a reagent of the present invention capable of localizing at sites of cancer due to an interaction between the biologically active group, Q, of the radiopharmaceutical and a receptor or binding site expressed at the site of the cancer or with a receptor or binding site on an endogenous blood component that accumulates at the site; (2) administering said radiopharmaceutical to a patient by injection or infusion; (3) imaging the patient using either planar or SPECT gamma scintigraphy.

The radiopharmaceuticals are administered by intravenous injection, usually in saline solution, at a dose of 1 to 100 mCi per 70 kg body weight, or preferably at a dose of 5 to 50 mCi. Imaging is performed using known procedures.

EXAMPLE SECTION

The materials used to synthesize the radiopharmaceuticals of the present invention described in the following examples were obtained as follows. The reagent of Formula 2, Cyclo(D-Val-NMeArg-Gly-Asp-Mamb(hydrazino-nicotinyl-5-Aca)) was synthesized as described in co-pending U.S. Ser. No. 08/218,861 (equivalent to WO 94/22494). The ancillary ligands tricine, tris(1-pyrazoyl)borohydride, imidazole, 2-methyl-5-nitroimidazole, ornidazole, metronidazole, 1,2,4-triazole, 3-nitro-1,2,4-triazole, acetyl histamine, urocanic acid, 2-methylimidazoline, 4-methyl-5-thiazoleethanol, tris(3,5-dimethyl-1-pyrazolyl)borohydride, adenosine, 8-hydroxyquinoline-5-sulfonic acid, and stannous chloride were obtained from commercial sources and used as received. Deionized water was obtained from a Milli-Q Water System and was of >18 MΩ quality. Technetium-99m-pertechnetate ($^{99m}TcO_4^-$) was obtained from a DuPont Pharma $^{99}Mo/^{99m}Tc$ generator.

Example 1

Synthesis of $^{99m}Tc$(tricine) (tris(1-pyrazolyl)borohydride)-Cyclo(D-Val-NMeArg-Gly-Asp-Mamb(hydrazino-nicotinyl-5-Aca))

To a 10 mL vial was added 0.4 mL of $^{99m}TcO_4^-$ (100 mCi/mL) eluent, followed by 0.1 mL of Cyclo(D-Val-NMeArg-Gly-Asp-Mamb(hydrazino-nicotinyl-5-Aca)) (100 μg/mL) in saline, 0.3 mL of tricine (100 mg/mL, pH 7), and 10 μL of SnCl$_2$ (10 mg/mL) in 1N HCl . The reaction mixture was heated at 50° C. for 15 min. To the reaction solution above was added 0.25 mL of tris(1-pyrazolyl)borohydride (20 mg/mL) in saline. The mixture was heated at 50° C. for 30 min, and was then analyzed by HPLC Method 1.

Example 2
Synthesis of $^{99m}$Tc(tricine) (imidazole)-Cyclo(D-Val-NMeArg-Gly-Asp-Mamb(hydrazino-nicotinyl-5-Aca))

To a 10 mL vial was added 0.3 mL of $^{99m}$TcO$_4^-$ solution (100 mCi/mL) in saline, 0.4 mL of tricine solution (100 mg/mL, pH~5.0) in H$_2$O, 0.1 mL of Cyclo(D-Val-NMeArg-Gly-Asp-Mamb(hydrazino-nicotinyl-5-Aca))solution (100 µg/mL) in H$_2$O, and 10 µL of SnCl$_2$.2H$_2$O solution (10 mg/mL) in 1.0N HCl. The reaction mixture was allowed to stand at room temperature for 15 min. After addition of 0.4 mL of imidazole solution (10 mg/mL) in H$_2$O, the reaction mixture was heated at 70° C. for 30 min, and was then analyzed by HPLC Method 1.

Example 3
Synthesis of $^{99m}$Tc(tricine) (1,2,4-triazole)-Cyclo(D-Val-NMeArg-Gly-Asp-Mamb(hydrazino-nicotinyl-5-Aca))

To a 10 mL vial was added 0.3 mL of $^{99m}$TcO$_4^-$ solution (100 mCi/mL) in saline, 0.4 mL of tricine solution (100 mg/mL, pH~5.0) in H$_2$O, 0.2 mL of Cyclo(D-Val-NMeArg-Gly-Asp-Mamb(hydrazino-nicotinyl-5-Aca)) solution (50 µg/mL) in H$_2$O, 0.2 mL of 3-nitro-1,2,4-triazole solution (30 mg/mL) in H$_2$O, and 5 µL of SnCl$_2$.2H$_2$O solution (10 mg/mL) in 1.0N HCl. The reaction mixture was heated at 75° C. for 25 min, and was then analyzed by HPLC Method 1.

Example 4
Synthesis of $^{99m}$Tc(tricine) (3-nitro-1,2,4-triazole)-Cyclo(D-Val-NMeArg-Gly-Asp-Mamb(hydrazino-nicotinyl-5-Aca))

To a 10 mL vial was added 0.3 mL of $^{99m}$TcO$_4^-$ solution (100 mCi/mL) in saline, 0.4 mL of tricine solution (100 mg/mL, pH~5.0) in H$_2$O, 0.2 mL of Cyclo(D-Val-NMeArg-Gly-Asp-Mamb(hydrazino-nicotinyl-5-Aca) solution (50 µg/mL) in H$_2$O, 0.2 mL of 3-nitro-1,2,4-triazole solution (30 mg/mL) in H$_2$O, and 5 µL of SnCl$_2$.2H$_2$O solution (10 mg/mL) in 1.0N HCl. The reaction mixture was heated at 75° C. for 25 min, and was then analyzed by HPLC Method 1.

Example 5
Synthesis of $^{99m}$Tc(tricine) (acetyl histamine)-Cyclo(D-Val-NMeArg-Gly-Asp-Mamb(hydrazino-nicotinyl-5-Aca))

To a 10 mL vial was added 0.4 mL of $^{99m}$TcO$_4^-$ (100 mCi/mL) eluent, followed by 0.2 mL of Cyclo(D-Val-NMeArg-Gly-Asp-Mamb(hydrazino-nicotinyl-5-Aca)) (50 µg/mL) in saline, 0.3 mL of tricine (100 mg/mL, pH 7), and 10 µL of SnCl$_2$ (10 mg/mL) in 1N HCl. The reaction mixture was heated at 55° C. for 15 min. To the reaction solution above was added 0.5 mL of acetyl histamine (20 mg/mL) in H$_2$O. The mixture was heated at 55° C. for 60 min, and was then analyzed by HPLC Method 1.

Example 6
Synthesis of $^{99m}$Tc(tricine) (metronidazole)-Cyclo(D-Val-NMeArg-Gly-Asp-Mamb(hydrazino-nicotinyl-5-Aca))

To a 10 mL vial was added 0.4 mL of $^{99m}$TcO$_4^-$ solution (100 mCi/mL) in saline, 0.3 mL of tricine solution (100 mg/mL, pH~5.0) in H$_2$O, 0.2 mL of Cyclo(D-Val-NMeArg-Gly-Asp-Mamb(hydrazino-nicotinyl-5-Aca)) solution (50 µg/mL) in H$_2$O, and 10 µL of SnCl$_2$.2H$_2$O solution (10 mg/mL) in 1.0N HCl. The reaction mixture was heated at 50° C. for 30 min. After addition of 0.5 mL of metrornidazole solution (20 mg/mL) in H$_2$O, the reaction mixture was heated at 70° C. for 30 min, and was then analyzed by HPLC Method 1.

Example 7
Synthesis of $^{99m}$Tc(tricine) (2-methylimidazoline)-Cyclo(D-Val-NMeArg-Gly-Asp-Mamb(hydrazino-nicotinyl-5-Aca))

To a 10 mL vial was added 0.4 mL of $^{99m}$TcO$_4^-$ (100 mCi/mL) eluent, followed by 0.2 mL of Cyclo(D-Val-NMeArg-Gly-Asp-Mamb(hydrazino-nicotinyl-5-Aca)) (50 µg/mL) in saline, 0.3 mL of tricine (100 mg/mL, pH 7), and 10 µL of SnCl$_2$ (10 mg/mL) in 1N HCl. The reaction mixture was heated at 50° C. for 15 min. To the reaction solution above was added 0.5 mL of 2-methylimidazoline (20 mg/mL) in in saline. The mixture was heated at 55° C. for 60 min, and was then analyzed by HPLC Method 1.

Example 8
Synthesis of $^{99m}$Tc(tricine) (3-pyridinesulfonic acid)(Cyclo(D-Val-NMeArg-Gly-Asp-Mamb(hydrazino-nicotinyl-5-Aca))

To a 10 mL vial was added 0.4 mL of tricine solution (100 mg/mL, pH 5.0) in H$_2$O, 0.4 mL of Cyclo(D-Val-NMeArg-Gly-Asp-Mamb(hydrazino-nicotinyl-5-Aca) solution (50 µg/mL) in H$_2$O, 0.2 mL of 3-pyridinesulfonic acid solution (10 mg/mL) in H$_2$O, 0.3 mL of $^{99m}$TcO$_4^-$ solution (100 mCi/mL) in saline, and 25 µL of SnCl$_2$.2H$_2$O solution (10 mg/mL) in 0.1N HCl.
The mixture was heated at 80° C. for 20 min, and was then analyzed by HPLC Method 2.

Example 9
Synthesis of $^{99m}$Tc(tricine) (4-methyl-5-thiazoleethanol)-Cyclo(D-Val-NMeArg-Gly-Asp-Mamb(hydrazino-nicotinyl-5-Aca))

To a 10 mL vial was added 0.4 mL of $^{99m}$TcO$_4^-$ (100 mCi/mL) eluent, followed by 0.2 mL of Cyclo(D-Val-NMeArg-Gly-Asp-Mamb(hydrazino-nicotinyl-5-Aca)) (50 µg/mL) in saline, 0.3 mL of tricine (100 mg/mL, pH 7), and 10 µL of SnCl$_2$ (10 mg/mL) in 1N HCl. The reaction mixture was heated at 50° C. for 30 min. To the reaction solution above was added 0.5 mL of 4-methylthiazoleethanol (10 mg/mL) in in saline. The mixture was heated at 75° C. for 30 min, and was then analyzed by HPLC Method 1.

Example 10
Synthesis of $^{99m}$Tc(tricine) (tris(3,5-dimethylpyrazolyl)borohydride)-Cyclo(D-Val-NMeArg-Gly-Asp-Mamb(hydrazino-nicotinyl-5-Aca))

To a 10 mL vial was added 0.2 mL of $^{99m}$TcO$_4^-$ (100 mCi/mL) eluent, followed by 0.2 mL of Cyclo(D-Val-NMeArg-Gly-Asp-Mamb(hydrazino-nicotinyl-5-Aca)) (50 µg/mL) in saline, 0.4 mL of tricine (100 mg/mL, pH 7), 0.2 mL of tris(3,5-dimethylpyrazoly)borohydride (20 mg/mL) in saline, and 10 µL of SnCl$_2$ (10 mg/mL) in 1N HCl. The mixture was heated at 75° C. for 30 min, and was then analyzed by HPLC Method 1.

Example 11
Synthesis of $^{99m}$Tc(tricine) (4-pyridineethanesulfonic acid)(Cyclo(D-Val-NMeArg-Gly-Asp-Mamb(hydrazino-nicotinyl-5-Aca))

To a 10 mL vial was added 0.4 mL of tricine solution (100 mg/mL, pH 5.0) in H$_2$O, 0.4 mL of Cyclo(D-Val-NMeArg-Gly-Asp-Mamb(hydrazino-nicotinyl-5-Aca)) (50 µg/mL) in H$_2$O, 0.4 mL of 4-pyridineethanesulfonic acid solution (35 mg/mL) in H$_2$O, 0.2 mL of $^{99m}$TcO$_4^-$ solution (250 mCi/mL) in saline, and 25 µL of SnCl$_2$.2H$_2$O solution (10 mg/mL) in 0.1N HCl. The reaction mixture was heated at 80° C. for 20 min, and was then analyzed by HPLC Method 1.

Example 12
Synthesis of $^{99m}$Tc(tricine) (ornidazole)-Cyclo(D-Val-NMeArg-Gly-Asp-Mamb(hydrazino-nicotinyl-5-Aca))

To a 10 mL vial was added 0.4 mL of $^{99m}TcO_4^-$ solution (100 mCi/mL) in saline, 0.2 mL of tricine solution (100 mg/mL, pH~5.0) in $H_2O$, 0.2 mL of Cyclo(D-Val-NMeArg-Gly-Asp-Mamb(hydrazino-nicotinyl-5-Aca)) solution (50 µg/mL) in $H_2O$, and 10 µL of $SnCl_2.2H_2O$ solution (10 mg/mL) in 1.0N HCl. The reaction mixture was allowed to stand at room temperature for 20 min. After addition of 0.5 mL of ornidazole solution (20 mg/mL) in $H_2O$, the reaction mixture was heated at 70° C. for 30 min, and was then analyzed by HPLC Method 1.

Example 13

Synthesis of $^{99m}Tc$(tricine) (4-(3H) pyrimidone) (Cyclo(D-Val-NMeArg-Gly-Asp-Mamb(hydrazino-nicotinyl-5-Aca))

To a 10 mL vial was added 0.4 mL of tricine solution (100 mg/mL, pH 5.0) in $H_2O$, 0.4 mL of Cyclo(D-Val-NMeArg-Gly-Asp-Mamb(hydrazino-nicotinyl-5-Aca) (50 µg/mL) in $H_2O$, 0.2 mL of 4-(3H)pyrimidone solution (10 mg/mL) in $H_2O$, 0.3 mL of $^{99m}TcO_4^-$ solution (100 mCi/mL) in saline, and 25 µL of $SnCl_2.2H_2O$ solution (10 mg/mL) in 0.1N HCl. The reaction mixture was heated at 80° C. for 20 min, and was then analyzed by HPLC Method 2.

Example 14

Synthesis of $^{99m}Tc$(tricine) (2-methyl-5-nitroimidazole)-Cyclo(D-Val-NMeArg-Gly-Asp-Mamb(hydrazino-nicotinyl-5-Aca))

To a 10 mL vial was added 0.4 mL of $^{99m}TcO_4^-$ solution (100 mCi/mL) in saline, 0.2 mL of tricine solution (100 mg/mL, pH~5.0) in $H_2O$, 0.2 mL of Cyclo(D-Val-NMeArg-Gly-Asp-Mamb(hydrazino-nicotinyl-5-Aca)) solution (50 µg/mL) in $H_2O$, and 10 µL of $SnCl_2.2H_2O$ solution (10 mg/mL) in 1.0N HCl. The reaction mixture was allowed to stand at room temperature for 15 min. After addition of 0.2 mL of 2-methyl-5-nitroimidazole solution (10 mg/mL) in $H_2O$, the reaction mixture was heated at 70° C. for 30 min, and was then analyzed by HPLC Method 1.

TABLE 1

Analytical and Yield Data on Ternary Complexes

| Example | Retention Time (min) | % Yield |
|---|---|---|
| 1 | 11.8 | 91 |
| 2 | 12.1, 12.5 | 86 |
| 3 | 12.7, 12.9 | 99 |
| 4 | 13.0, 13.2 | 95 |
| 5 | 12.6 | 97 |
| 6 | 14.4 | 89 |
| 7 | 12.3 | 97 |
| 8 | 8.8* | 91 |
| 9 | 13.4 | 92 |
| 10 | 14.9, 15.5 | 89 |
| 11 | 12.4 | 90 |
| 12 | 16.0, 16.5 | 81 |
| 13 | 8.1, 8.5* | 89 |
| 14 | 12.8 | 71 |

*Data from Method 2; the others are from Method 1.

The values reported in Table 1 were obtained using HPLC Methods 1 or 2. One retention time is shown for most of these examples. The two isomers that comprise these radiopharmaceuticals are usually not completely resolved by these HPLC methods. Typically there is a shoulder on the main peak reported.

Analytical Methods

HPLC Methods 1
Column: Vydac $C_{18}$ (4.6 mm×25 cm)
Flow rate: 1 mL/min

Solvent A=0.01M pH 6 phosphate buffer
Solvent B=acetonitrile
Gradient:

| t = 0 min | 100% A |
| t = 15 min | 70% A, 30% B |
| t = 25 min | 25% A, 75% B |

Detection by sodium iodide probe

HPLC Method 2
Column: Zorbax Rx $C_{18}$ (4.6 mm×25 cm)
Flow rate: 1 mL/min
Solvent A=90:10 0.025M pH 8 phosphate buffer:acetonitrile
Solvent B=50:50 0.025M pH 8 phosphate buffer:acetonitrile
Gradient:

| t = 0 min | 100% A |
| t = 25 min | 100% B |

Detection by sodium iodide probe

Utility

The radiopharmaceuticals provided herein are useful as imaging agents for the diagnosis of cardiovascular disorders, such as thromboembolic disease or atherosclerosis, infectious disease and cancer. The radiopharmaceuticals are comprised of technetium-99m labeled hydrazino or diazenido modified biologically active molecules that selectively localize at sites of disease and thus allow an image to be obtained of the loci using gamma scintigraphy.

Canine Deep Vein Thrombosis Model: This model incorporates the triad of events (hypercoagulatible state, period of stasis, low shear environment) essential for the formation of a venous fibrin-rich actively growing thrombus. The procedure was as follows: Adult mongrel dogs of either sex (9–13 kg) were anesthetized with pentobarbital sodium (35 mg/kg, i.v.) and ventilated with room air via an endotracheal tube (12 strokes/min, 25 ml/kg). For arterial pressure determination, the right femoral artery was cannulated with a saline-filled polyethylene catheter (PE-240) and connected to a Statham pressure transducer (P23ID; Oxnard, Calif.). Mean arterial blood pressure was determined via damping the pulsatile pressure signal. Heart rate was monitored using a cardiotachometer (Biotach, Grass Quincy, Mass.) triggered from a lead II electrocardiogram generated by limb leads. The right femoral vein was cannulated (PE-240) for drug administration. A 5 cm segment of both jugular veins was isolated, freed from fascia and circumscribed with silk suture. A microthermister probe was placed on the vessel which serves as an indirect measure of venous flow. A balloon embolectomy catheter was utilized to induce the 15 min period of stasis during which time a hypercoagulatible state was then induced using 5 U thrombin (American Diagnosticia, Greenwich Conn.) administered into the occluded segment. Fifteen minutes later, flow was reestablished by deflating the balloon. The radiopharmaceutical was infused during the first 5 minutes of reflow and the rate of incorporation monitored using gamma scintigraphy.

Canine Arteriovenous Shunt Model: Adult mongrel dogs of either sex (9–13 kg) were anesthetized with pentobarbital sodium (35 mg/kg,i.v.) and ventilated with room air via an endotracheal tube (12 strokes/min, 25 ml/kg). For arterial pressure determination, the left carotid artery was cannulated with a saline-filled polyethylene catheter (PE-240) and connected to a Statham pressure transducer (P23ID; Oxnard, Calif.). Mean arterial blood pressure was determined via damping the pulsatile pressure signal. Heart rate was monitored using a cardiotachometer (Biotach, Grass Quincy, Mass.) triggered from a lead II electrocardiogram generated by limb leads. A jugular vein was cannulated (PE-240) for drug administration. The both femoral arteries and femoral veins were cannulated with silicon treated (Sigmacote, Sigma Chemical Co. St Louis, Mo.), saline filled polyethylene tubing (PE-200) and connected with a 5 cm section of silicon treated tubing (PE-240) to form an extracorporeal arterio-venous shunts (A-V). Shunt patency was monitored using a doppler flow system (model VF-1, Crystal Biotech Inc, Hopkinton, Mass.) and flow probe (2–2.3 mm, Titronics Med. Inst., Iowa City, Iowa) placed proximal to the locus of the shunt. All parameters were monitored continuously on a polygraph recorder (model 7D Grass) at a paper speed of 10 mm/min or 25 mm/sec.

On completion of a 15 min post surgical stabilization period, an occlusive thrombus was formed by the introduction of a thrombogenic surface ( 4–0 braided silk thread, 5 cm in length, Ethicon Inc., Somerville, N.J.) into the shunt one shunt with the other serving as a control. Two consecutive 1 hr shunt periods were employed with the test agent administered as an infusion over 5 min beginning 5 min before insertion of the thrombogenic surface. At the end of each 1 hr shunt period the silk was carefully removed and weighed and the % incorporation determined via well counting. Thrombus weight was calculated by subtracting the weight of the silk prior to placement from the total weight of the silk on removal from the shunt. Arterial blood was withdrawn prior to the first shunt and every 30 min thereafter for determination of blood clearance, whole blood collagen-induced platelet aggregation, thrombin-induced platelet degranulation (platelet ATP release), prothrombin time and platelet count. Template bleeding time was also performed at 30 min intervals.

Complexes in which the biologically active molecules, Q, are chemotactic peptides can be evaluated for potential clinical utility as radiopharmaceuticals for the diagnosis of infection by performing imaging studies in a guinea pig model of focal infection.

Guinea Pig Focal Infection Model: Hartley guinea pigs; unspecified sex; weight between 200–250 grams are fasted overnight prior to the procedure. Each guinea pig is anesthetized with a mixture of ketamine 25–55 mg/kg//IM and xylazine 2–5 mg/kg/IM. A #10 trochar needle is used to introduce a 2 inch piece of umbilical string that has been immersed in a 6% sodium caseinate solution (this is the chemoattractant) into the right flank and is placed on the left side of the peritoneal cavity. The placement of the chemoattractant serves as a focal site for white blood cell recruitment. The puncture site is sealed with Nexabain, a skin glue (if required). The animals are allowed to recover for 18 hrs.

Eighteen hours later the guinea pigs are anesthetized with kettamine 25–55 mg/kg//IM and xylazine 2–5 mg/kg/IM to achieve Stage III/Plane III of anesthesia and insure proper injection of the test agent into the lateral saphenous vein. Once the test agent is administered the guinea pigs are placed behind a lead shield and monitored for 1–4 hours. At the appropriate time postinjection, the animals are euthanized with pentobarbital sodium 65 mg/kg, I.V. and a biodistribution performed. Throughout the course of the study, blood samples are withdrawn via cardiac puncture.

Results

Figure 1B:
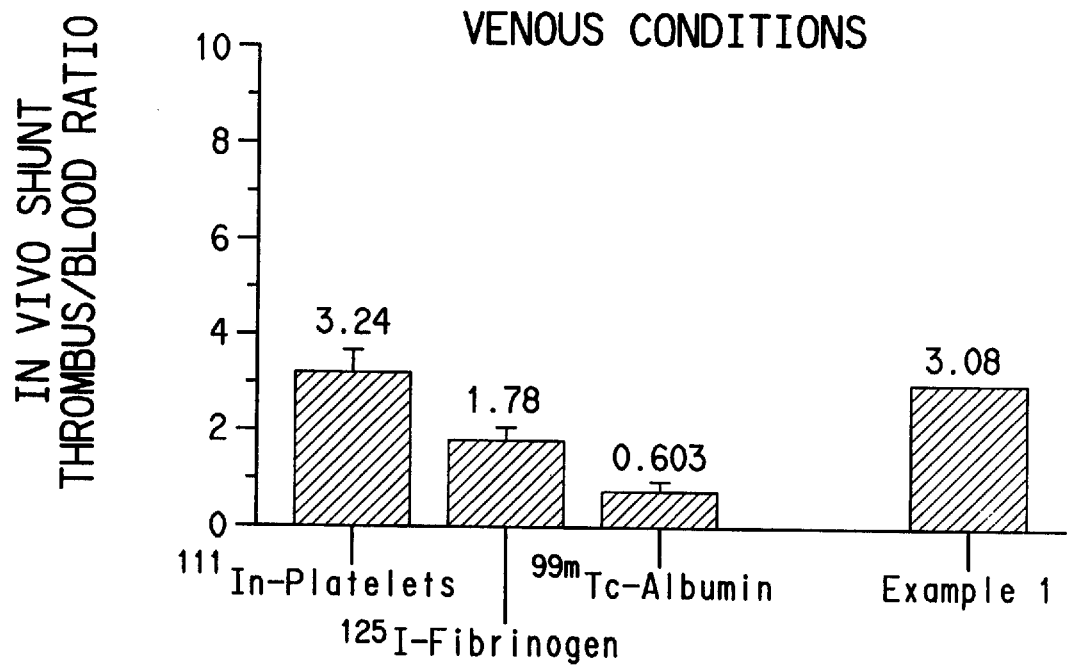
Figure 1C:
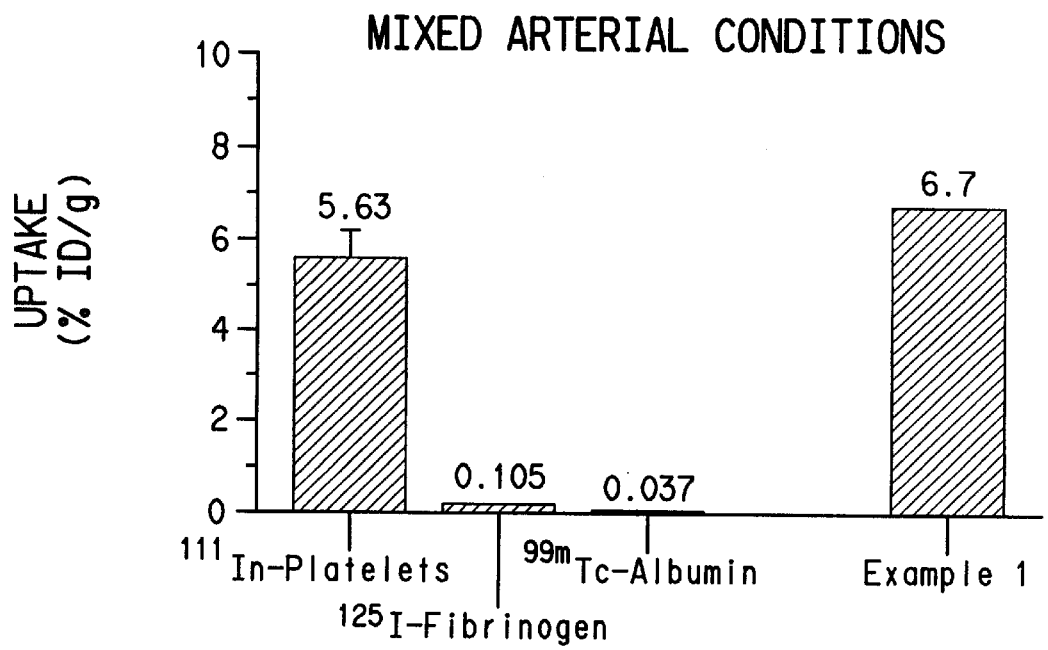
Figure 1D:
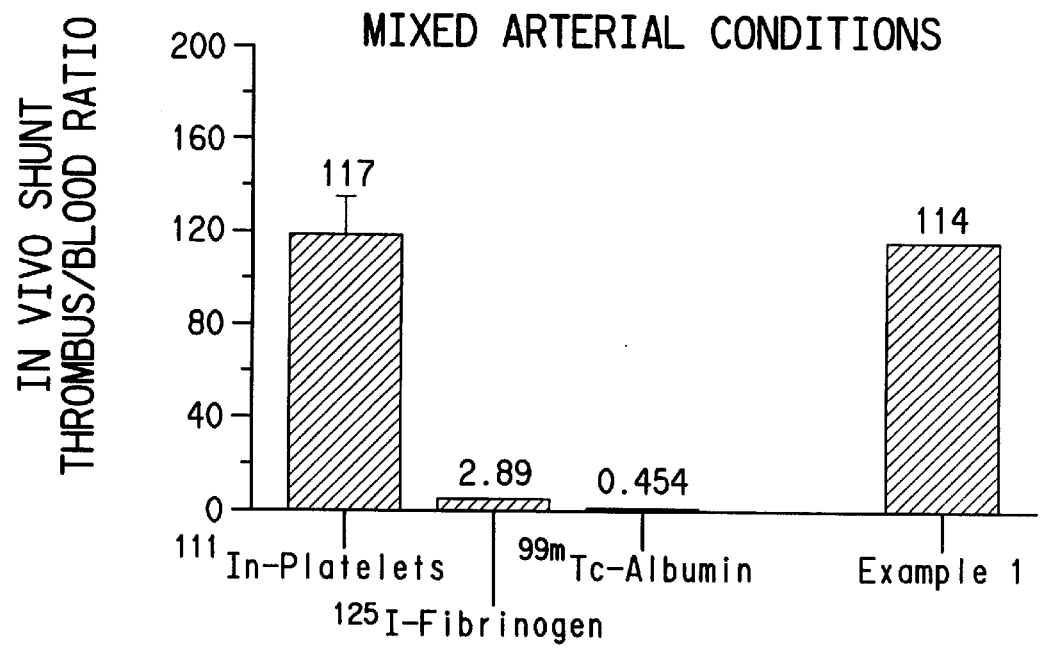

The results of the evaluation of the radiopharmaceutical of Example 1 in the Canine Arteriovenous Shunt model is shown in FIG. 1. Included are results for the positive control, In-111-labeled autologous platelets and the negative controls, Tc-99m-albumin and I-125-fibrinogen. All values are for the first 1 hour shunt period. The data show that the radiopharmaceutical of Example 1 is taken up in thrombi under both mixed arterial and venous conditions equivalently to the positive control and to a significantly greater extent than the negative controls. The thrombus-to-blood ratios (target-to-background ratios), 114 (mixed arterial) and 3.1 (venous) indicate that the thrombi can be readily differentiated from the surrounding tissue and fluid by standard imaging techniques familiar to those skilled in the art. The important advantage of the radiopharmaceutical of Example 1 over the positive control, In-111-platelets, is that the laborious extracorporeal labeling procedure used to label autologous platelets with In-111 is not necessary. This shortens the time needed to obtain diagnostic information and avoids the potential risk of exposure of the nuclear medicine practitioner to blood-borne pathogens, such as HIV.

We claim:

1. A radiopharmaceutical of the formula:

$$[(Q)_{d'}L_n—C_{h'}]_k—M_t(A_{L1})_y(A_{L2})_z$$

or a pharmaceutically acceptable salt thereof wherein,

Q is a biologically active group;

d' is 1 to 20;

$L_n$ is a linking group of formula:

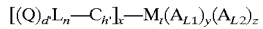

$M^1$ is $—[(CH_2)_gZ^1]_{g'}—(CR^{55}R^{56})_{g''}—$;

$M^2$ is $—(CR^{55}R^{56})_{g''}—[Z^1(CH_2)_g]_{g'}—$;

g is independently 0–10;

g' is independently 0–1;

g'' is independently 0–10;

f is independently 0–10;

f' is independently 0–10;

f'' is independently 0–1;

$Y^1$ and $Y^2$, at each occurrence, are independently selected from the group consisting of: a bond, O, $NR^{56}$, C=O, C(=O)O, OC(=O)O, C(=O)NH—, C=$NR^{56}$, S, SO, $SO_2$, $SO_3$, NHC(=O), $(NH)_2C(=O)$, and $(NH)_2C=S$;

$Z^1$ is independently selected at each occurrence from the group consisting of: a $C_6–C_{14}$ saturated, partially saturated, or aromatic carbocyclic ring system, substituted with 0–4 $R^{57}$; and a heterocyclic ring system, optionally substituted with 0–4 $R^{57}$;

$R^{55}$ and $R^{56}$ are independently selected at each occurrence from the group consisting of: hydrogen, $C_1–C_{10}$ alkyl substituted with 0–5 $R^{57}$, and alkaryl wherein the aryl is substituted with 0–5 $R^{57}$;

$R^{57}$ is independently selected at each occurrence from the group consisting of: hydrogen, OH, $NHR^{58}$, C(=O)$R^{58}$, OC(=O)$R^{58}$, OC(=O)O$R^{58}$, C(=O)O$R^{58}$, C(=O)NR$^{58}$, C=N, SR$^{58}$, SOR$^{58}$, SO$_2$R$^{58}$, NHC(=O)R$^{58}$, NHC(=O)NHR$^{58}$, and NHC(=S)NHR$^{58}$;

alternatively, when attached to an additional molecule Q, $R^{57}$ is independently selected at each occurrence from the group consisting of: O, $NR^{58}$, C=O, C(=O)O, OC(=O)O, C(=O)N, C=$NR^{58}$, S, SO, $SO_2$, $SO_3$, NHC(=O), $(NH)_2C(=O)$, and $(NH)_2C=S$;

$R^{58}$ is independently selected at each occurrence from the group consisting of: hydrogen, $C_1–C_6$ alkyl, benzyl, and phenyl;

x, y and z are independently 1 or 2;

$M_t$ is a transition metal radionuclide selected from the group consisting of: $^{99m}$Tc, $^{186}$Re and $^{188}$Re;

$C_{h'}$ is a radionuclide metal chelator coordinated to transition metal radionuclide $M_t$, and is independently selected at each occurrence from the group consisting of: $R^{40}N=N^+=$, $R^{40}R^{41}N—N=$, and $R^{40}N=N(H)—$;

$R^{40}$ is independently selected at each occurrence from the group consisting of: a bond to $L_n$, $C_1$–$C_{10}$ alkyl substituted with 0–3 $R^{52}$, aryl substituted with 0–3 $R^{52}$, cycloalkyl substituted with 0–3 $R^{52}$, heterocycle substituted with 0–3 $R^{52}$, heterocycloalkyl substituted with 0–3 $R^{52}$, aralkyl substituted with 0–3 $R^{52}$ and alkaryl substituted with 0–3 $R^{52}$;

$R^{41}$ is independently selected from the group consisting of: hydrogen, aryl substituted with 0–3 $R^{52}$, $C_1$–$C_{10}$ alkyl substituted with 0–3 $R^{52}$, and a heterocycle substituted with 0–3 $R^{52}$;

$R^{52}$ is independently selected at each occurrence from the group consisting of: a bond to $L_n$, $=O$, F, Cl, Br, I, $—CF_3$, $—CN$, $—CO_2R^{53}$, $—C(=O)R^{53}$, $—C(=O)N(R^{53})_2$, $—CHO$, $—CH_2O\ R^{53}$, $—OC(=O)R^{53}$, $—OC(=O)OR^{53a}$, $—OR^{53}$, $—OC(=O)N(R^{53})_2$, $—NR^{53}C(=O)R^{53}$, $—N(R^{53})_3^+$, $—NR^{54}C(=O)OR^{53a}$, $—NR^{53}C(=O)N(R^{53})_2$, $—NR^{54}SO_2N(R^{53})_2$, $—NR^{54}SO_2R^{53a}$, $—SO_3H$, $—SO_2R^{53a}$, $—SR^{53}$, $—S(=O)R^{53a}$, $—SO_2N(R^{53})_2$, $—N(R^{53})_2$, $—NHC(=NH)NHR^{53}$, $—C(=NH)NHR^{53}$, $=NOR^{53}$, $NO_2$, $—C(=O)NHOR^{53}$, $—C(=O)NHNR^{53}R^{53a}$, $—OCH_2CO_2H$, and 2-(1-morpholino)ethoxy;

$R^{53}$, $R^{53a}$, and $R^{54}$ are each independently selected at each occurrence from the group consisting of: hydrogen, $C_1$–$C_6$ alkyl, and a bond to $L_n$;

$A_{L1}$ is a first ancillary ligand selected from the group consisting of: dioxygen ligand and functionalized aminocarboxylate;

$A_{L2}$ is an ancillary ligand capable of stabilizing the radiopharmaceutical selected from the group consisting of:

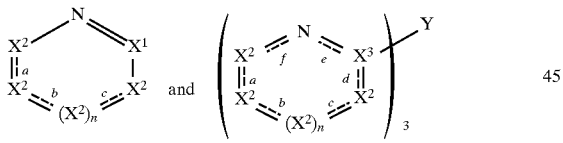

n is 0 or 1;

$X^1$ is independently selected at each occurrence from the group consisting of: $CR^{64}$ and N;

$X^2$ is independently selected at each occurrence from the group consisting of: $CR^{64}$, $CR^{64}R^{64}$, N, $NR^{64}$, O and S;

$X^3$ is independently selected at each occurrence from the group consisting of: C, $CR^{64}$, and N;

provided the total number of heteroatoms in each ring of the ligand $A_{L2}$ is 1 to 4;

Y is selected from the group consisting of: $BR^{64-}$, $CR^{64}$, (P=O), and (P=S);

and a, b, c, d, e and f indicate the positions of optional double bonds, provided that one of e and f is a double bond;

$R^{64}$ is independently selected at each occurrence from the group consisting of: H, $C_1$–$C_{10}$ alkyl substituted with 0–3 $R^{65}$, $C_2$–$C_{10}$ alkenyl substituted with 0–3 $R^{65}$, $C_2$–$C_{10}$ alkynyl substituted with 0–3 $R^{65}$, aryl substituted with 0–3 $R^{65}$, carbocycle substituted with 0–3 $R^{65}$, and $R^{65}$;

alternatively, two $R^{64}$ may be taken together with the atom or atoms to which they are attached to form a fused aromatic, carbocyclic or heterocyclic ring, substituted with 0–3 $R^{65}$;

$R^{65}$ is independently selected at each occurrence from the group consisting of: $=O$, F, Cl, Br, I, $—CF_3$, $—CN$, $—NO_2$, $—CO_2R^{66}$, $—C(=O)R^{66}$, $—C(=O)N(R^{66})_2$, $—N(R^{66})_3^+$, $—CH_2OR^{66}$, $—OC(=O)R^{66}$, $—OC(=O)OR^{66a}$, $—OR^{66}$, $—OC(=O)N(R^{66})_2$, $—NR^{66}C(=O)R^{66}$, $—NR^{67}C(=O)OR^{66a}$, $—NR^{66}C(=O)N(R^{66})_2$, $—NR^{67}SO_2N(R^{66})_2$, $—NR^{67}SO_2R^{66a}$, $—SO_3H$, $—SO_2R^{66a}$, $—SO_2N(R^{66})_2$, $—N(R^{66})_2$, and $—OCH_2CO_2H$; and, $R^{66}$, $R^{66a}$, and $R^{67}$ are each independently selected at each occurrence from the group consisting of: hydrogen and $C_1$–$C_6$ alkyl.

2. The radiopharmaceutical of claim 1 wherein:

Q is a biologically active molecule selected from the group consisting of: IIb/IIIa receptor antagonists, IIb/IIIa receptor ligands, fibrin binding peptides, leukocyte binding peptides, chemotactic peptides, somatostatin analogs, and selectin binding peptides;

d' is 1 to 3;

$L_n$ is:

$—(CR^{55}R^{56})_{g''}—[Y^1(CR^{55}R^{56})_fY^2]_{f'}—(CR^{55}R^{56})_{g'}—$, g" is 0–5;

f is 0–5;

f' is 1–5;

$Y^1$ and $Y^2$, at each occurrence, are independently selected from the group consisting of: O, $NR^{56}$, $C=O$, $C(=O)O$, $OC(=O)O$, $C(=O)NH$, $C=NR^{56}$, S, SO, $SO_2$, $SO_3$, $NHC(=O)$, $(NH)_2C(=O)$, and $(NH)_2C=S$;

$R^{55}$ and $R^{56}$ are independently selected at each occurrence from the group consisting of: hydrogen, $C_1$–$C_{10}$ alkyl and alkaryl;

x and y are 1;

$M_t$ is $^{99m}$Tc;

$C_{h'}$ is selected from the group consisting of: $R^{40}N=N^+=$ and $R^{40}R^{41}N—N=$;

$R^{40}$ is independently selected at each occurrence from the group consisting of: aryl substituted with 0–3 $R^{52}$ and heterocycle substituted with 0–3 $R^{52}$;

$R^{41}$ is independently selected from the group consisting of: hydrogen, aryl substituted with 0–1 $R^{52}$, $C_1$–$C_3$ alkyl substituted with 0–1 $R^{52}$, and a heterocycle substituted with 0–1 $R^{52}$;

$R^{52}$ is independently selected at each occurrence from the group consisting of: a bond to $L_n$, $—CO_2R^{53}$, $—CH_2OR^{53}$, $—SO_3H$, $—SO_2R^{53a}$, $—N(R^{53})_2$, $—N(R^{53})_3^+$, $—NHC(=NH)NHR^{53}$, and $—OCH_2CO_2H$;

$R^{53}$ and $R^{53a}$ are each independently selected at each occurrence from the group consisting of: hydrogen and $C_1$–$C_3$ alkyl;

$A_{L1}$ is a functionalized aminocarboxylate;

n is 0;

Y is $BR^{64-}$;

$R^{64}$ is independently selected at each occurrence from the group consisting of: H, $C_1$–$C_3$ alkyl substituted with 0–3 $R^{65}$, aryl substituted with 0–3 $R^{65}$, and $R^{65}$;

alternatively, two $R^{64}$ may be taken together with the atom or atoms to which they are attached to form a fused aromatic or heterocyclic ring, substituted with 0–3 $R^{65}$;

$R^{65}$ is independently selected at each occurrence from the group consisting of: $-NO_2$, $-CO_2R^{66}$, $-OR^{66}$, $-SO_3H$, and $-OCH_2CO_2H$; and, $R^{66}$ is hydrogen.

3. The radiopharmaceutical of claim 2 wherein:

Q is a biologically active molecule selected from the group consisting of: IIb/IIIa receptor antagonists and chemotactic peptides;

d' is 1;

$Y^1$ and $Y^2$, at each occurrence, are independently selected from the group consisting of: O, $NR^{56}$, C=O, C(=O)O, OC(=O)O, C(=O)NH, C=$NR^{56}$, NHC(=O), and $(NH)_2C(=O)$;

$R^{55}$ and $R^{56}$ are hydrogen;

z is 1;

$R^{40}$ is heterocycle substituted with $R^{52}$;

$R^{41}$ is hydrogen;

$R^{52}$ is a bond to $L_n$;

$A_{L1}$ is tricine;

$X^2$ is independently selected at each occurrence from the group consisting of: $CR^{64}$, $CR^{64}R^{64}$, N, $NR^{64}$ and O;

$X^3$ is N;

provided the total number of heteroatoms in each ring of the ligand $A_{L2}$ is 2 to 3;

$R^{64}$ is independently selected at each occurrence from the group consisting of: H, $C_1-C_3$ alkyl substituted with 0–1 $R^{65}$, aryl substituted with 0–1 $R^{65}$, and $R^{65}$; and, $R^{65}$ is independently selected at each occurrence from the group consisting of: $-NO_2$, $-CO_2R^{66}$, $-OR^{66}$, and $-SO_3H$.

4. The radiopharmaceutical of claim 1 wherein:

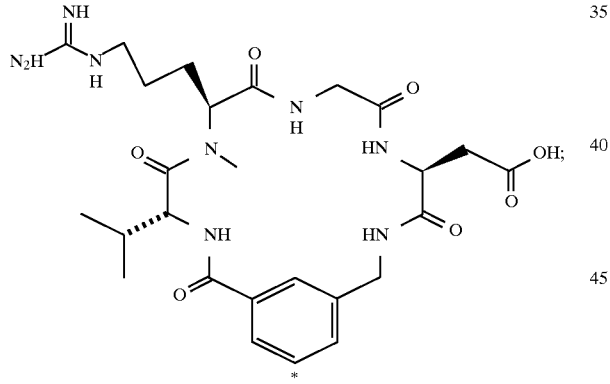

Q is d' is 1;

$L_n$ is attached to Q at the carbon atom designated with a * and has the formula:

$-(C=O)NH(CH_2)_5C(=O)NH-$;

$C_{h'}$ is

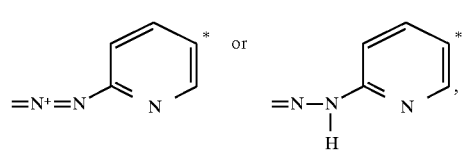

and is attached to $L_n$ at the carbon atom designated with a *;

$M_t$ is $^{99m}Tc$;

$A_{L1}$ is tricine;

x, y and z are 1;

and $A_{L2}$ is selected from the group consisting of:

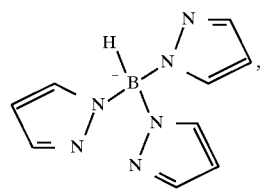

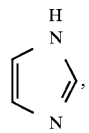

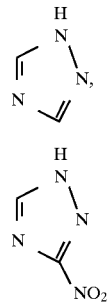

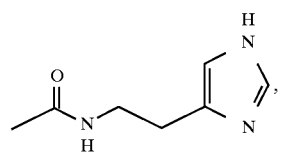

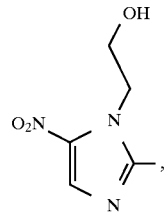

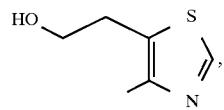

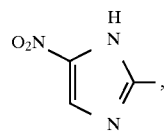

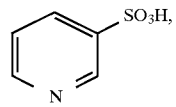

-continued

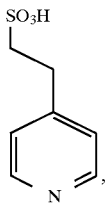

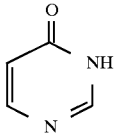

and

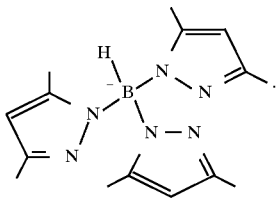

5. A method for radioimaging a mammal comprising (i) administering to said mammal an effective amount of a radiopharmaceutical of any of claims 1–4, and (ii) scanning the mammal using a radioimaging device.

6. A method for visualizing sites of platelet deposition in a mammal by radioimaging, comprising (i) administering to said mammal an effective amount of a radiopharmaceutical of any of claims 1–4, and (ii) scanning the mammal using a radioimaging device.

7. A method of determining platelet deposition in a mammal comprising administering to said mammal a radiopharmaceutical composition of any of claims 1–4, and imaging said mammal.

8. A method of diagnosing a disorder associated with platelet deposition in a mammal comprising administering to said mammal a radiopharmaceutical composition of any of claims 1–4, and imaging said mammal.

9. A kit for preparing a radiopharmaceutical comprising:

(a) a predetermined quantity of a sterile, pharmaceutically acceptable reagent of formula:

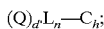

(b) a predetermined quantity of a sterile, pharmaceutically acceptable first ancillary ligand, $A_{L1}$, selected from the group consisting of: dioxygen ligand and functionalized aminocarboxylate;

(c) a predetermined quantity of a sterile, pharmaceutically acceptable second ancillary ligand, $A_{L2}$, selected from the group consisting of:

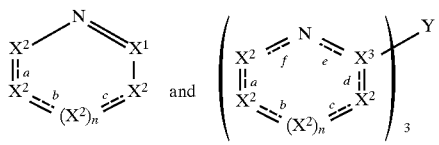

(d) a predetermined quantity of a sterile, pharmaceutically acceptable reducing agent; and (e) optionally, a predetermined quantity of one or more sterile, pharmaceutically acceptable components selected from the group consisting of: transfer ligands, buffers, lyophilization aids, stabilization aids, solubilization aids and bacteriostats;

wherein:

Q is a biologically active molecule;

d' is 1 to 20;

$L_n$ is a linking group of formula:

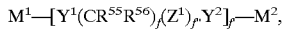
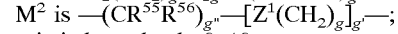

g is independently 0–10;
g' is independently 0–1;
g" is independently 0–10;
f is independently 0–10;
f' is independently 0–10;
f" is independently 0–1;

$Y^1$ and $Y^2$, at each occurrence, are independently selected from the group consisting of: a bond, O, $NR^{56}$, C=O, C(=O)O, OC(=O)O, C(=O)NH—, C=$NR^{56}$, S, SO, $SO_2$, $SO_3$, NHC(=O), $(NH)_2C(=O)$, and $(NH)_2C=S$;

$Z^1$ is independently selected at each occurrence from a $C_6$–$C_{14}$ saturated, partially saturated, or aromatic carbocyclic ring system, substituted with 0–4 $R^{57}$, and a heterocyclic ring system, optionally substituted with 0–4 $R^{57}$;

$R^{55}$ and $R^{56}$ are independently selected at each occurrence from the group consisting of: hydrogen; $C_1$–$C_{10}$ alkyl substituted with 0–5 $R^{57}$, and alkaryl wherein the aryl is substituted with 0–5 $R^{57}$;

$R^{57}$ is independently selected at each occurrence from the group consisting of: hydrogen, OH, $NHR^{58}$, C(=O)$R^{58}$, OC(=O)$R^{58}$, OC(=O)O$R^{58}$, C(=O)O$R^{58}$, C(=O)N$R^{58}$, C=N, $SR^{58}$, $SOR^{58}$, $SO_2R^{58}$, NHC(=O)$R^{58}$, NHC(=O)NHR$^{58}$, and NHC(=S)NHR$^{58}$;

alternatively, when attached to an additional molecule Q, $R^{57}$ is independently selected at each occurrence from the group consisting of: O, $NR^{58}$, C=O, C(=O)O, OC(=O)O, C(=O)N, C=$NR^{58}$, S, SO, $SO_2$, $SO_3$, NHC(=O), $(NH)_2C(=O)$, and $(NH)_2C=S$;

$R^{58}$ is independently selected at each occurrence from the group consisting of: hydrogen, $C_1$–$C_6$ alkyl, benzyl, and phenyl;

$C_h$ is a radionuclide metal chelator selected from the group consisting of: $R^{40}R^{41}$N—N=C($C_1$–$C_3$ alkyl)$_2$ and $R^{40}$NNH$_2$—, and $R^{40}R^{41}$N—N=C$R^{80}R^{81}$;

$R^{40}$ is independently selected at each occurrence from the group consisting of: a bond to $L_n$, $C_1$–$C_{10}$ alkyl substituted with 0–3 $R^{52}$, aryl substituted with 0–3 $R^{52}$, cycloaklyl substituted with 0–3 $R^{52}$, heterocycle substituted with 0–3 $R^{52}$, heterocycloalkyl substituted with 0–3 $R^{52}$, aralkyl substituted with 0–3 $R^{52}$ and alkaryl substituted with 0–3 $R^{52}$;

$R^{41}$ is independently selected from the group consisting of: hydrogen, aryl substituted with 0–3 $R^{52}$, $C_1$–$C_{10}$ alkyl substituted with 0–3 $R^{52}$, and a heterocycle substituted with 0–3 $R^{52}$;

$R^{52}$ is independently selected at each occurrence from the group consisting of: a bond to $L_n$, =O, F, Cl, Br, I, —CF$_3$, —CN, —CO$_2$R$^{53}$, —C(=O)

$R^{53}$, —C(=O)N($R^{53}$)$_2$, —CHO, —CH$_2$O$R^{53}$, —OC(=O)$R^{53}$, —OC(=O)O$R^{53a}$, —O$R^{53}$, —OC(=O)N($R^{53}$)$_2$, —N$R^{53}$C(=O)$R^{53}$, —N$R^{54}$C(=O)O$R^{53a}$, —N($R^{53}$)$_3^+$, —N$R^{53}$C(=O)N($R^{53}$)$_2$, —N$R^{54}$SO$_2$N($R^{53}$)$_2$, —N$R^{54}$SO$_2R^{53a}$, —SO$_3$H, SO$_2R^{53a}$, -S$R^{53}$, —S(=O)$R^{53a}$, —SO$_2$N($R^{53}$)$_2$, —N($R^{53}$)$_2$, —NHC(=NH)NH$R^{53}$, —C(=NH)NH$R^{53}$, =NO$R^{53}$, NO$_2$, —C(=O)NHO$R^{53}$, —C(=O)NHN$R^{53}R^{53a}$, —OCH$_2$CO$_2$H, and 2-(1-morpholino)ethoxy;

$R^{53}$, $R^{53a}$, and $R^{54}$ are each independently selected at each occurrence from the group consisting of: hydrogen, $C_1$–$C_6$ alkyl, and a bond to $L_n$;

$R^{80}$ and $R^{81}$ are independently selected from the group consisting of: H, $C_1$–$C_{10}$ alkyl, —CN, —CO$_2R^{85}$, —C(=O)$R^{85}$, —C(=O)N($R^{85}$)$_2$, $C_2$–$C_{10}$ 1-alkene substituted with 0–3 $R^{84}$, $C_2$–$C_{10}$ 1-alkyne substituted with 0–3 $R^{84}$, aryl substituted with 0–3 $R^{84}$, unsaturated heterocycle substituted with 0–3 $R^{84}$, and unsaturated carbocycle substituted with 0–3 $R^{84}$, provided that when one of $R^{80}$ and $R^{81}$ is H or alkyl, then the other is not H or alkyl;

or, alternatively, $R^{80}$ and $R^{81}$, may be taken together with the shown divalent carbon radical to form:

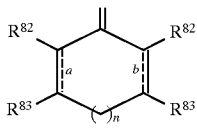

$R^{82}$ and $R^{83}$ may be independently selected from the group consisting of: H, $R^{84}$, $C_1$–$C_{10}$ alkyl substituted with 0–3 $R^{84}$, $C_2$–$C_{10}$ alkenyl substituted with 0–3 $R^{84}$, $C_2$–$C_{10}$ alkynyl substituted with 0–3 $R^{84}$, aryl substituted with 0–3 $R^{84}$, heterocycle substituted with 0–3 $R^{84}$ and carbocycle substituted with 0–3 $R^{84}$;

alternatively, $R^{82}$, $R^{83}$ may be taken together to form a fused aromatic or heterocyclic ring;

$R^{84}$ is independently selected at each occurrence from the group consisting of: =O, F, Cl , Br, I, —CF$_3$, —CN, —CO$_2R^{85}$, —C(=O)$R^{85}$, —C(=O)N($R^{85}$)$_2$, —N($R^{85}$)$_3^+$, —CH$_2$O$R^{85}$, —OC(=O) $R^{85}$, —OC(=O)O$R^{85a}$, —O$R^{85}$, —OC(=O)N($R^{85}$)$_2$, —N$R^{85}$C(=O)$R^{85}$, —N$R^{86}$C(=O)O$R^{85a}$, —N$R^{85}$C(=O)N($R^{85}$)$_2$, —N$R^{86}$SO$_2$N($R^{85}$)$_2$, —N$R^{86}$SO$_2R^{85a}$, —SO$_3$H, —SO$_2R^{85a}$, —S$R^{85}$, —S(=O)$R^{85a}$, —SO$_2$N ($R^{85}$)$_2$, —N($R^{85}$)$_2$, —NHC(=NH)NH$R^{85}$, —C(=NH)NH$R^{85}$, =NO$R^{85}$, —C(=O)NHO$R^{85}$, —OCH$_2$CO$_2$H, and 2-(1-morpholino)ethoxy; and $R^{85}$, $R^{85a}$, and $R^{86}$ are each independently selected at each occurrence from the group consisting of: hydrogen and $C_1$–$C_6$ alkyl $X^1$ is independently selected at each occurrence from the group consisting of: C$R^{64}$ and N;

$X^2$ is independently selected at each occurrence from the group consisting of: C$R^{64}$, C$R^{64}R^{64}$, N, N$R^{64}$, O and S;

$X^3$ is independently selected at each occurrence from the group consisting of: C, C$R^{64}$, and N;

Y is selected from the group consisting of: B$R^{64-}$, C$R^{64}$, (P=O), and (P=S);

provided the total number of heteroatoms in each ring of the heterocycle is 1 to 4;

$R^{64}$ is independently selected at each occurrence from the group consisting of: H, $C_1$–$C_{10}$ alkyl substituted with 0–3 $R^{65}$, $C_2$–$C_{10}$ alkenyl substituted with 0–3 $R^{65}$, $C_2$–$C_{10}$ alkynyl substituted with 0–3 $R^{65}$, aryl substituted with 0–3 $R^{65}$, carbocycle substituted with 0–3 $R^{65}$ and $R^{65}$;

alternatively, two $R^{64}$ may be taken together with the atom or atoms to which they are attached to form a fused aromatic, carbocyclic or heterocyclic ring, substituted with 0–3 $R^{65}$;

$R^{65}$ is independently selected at each occurrence from the group consisting of: =O, F, Cl, Br, I, —CF$_3$, —CN, —NO$_2$, —CO$_2R^{66}$, —C(=O)$R^{66}$, —C(=O)N($R^{66}$)$_2$, —N($R^{66}$)$_3^+$, —CH$_2$O$R^{66}$, —OC(=O)$R^{66}$, —OC(=O)O$R^{66a}$, —O$R^{66}$, —OC(=O)N($R^{66}$)$_2$, —N$R^{66}$C(=O)$R^{66}$, —N$R^{67}$C(=O)O$R^{66a}$, —N$R^{66}$C(=O)N($R^{66}$)$_2$, —N$R^{67}$SO$_2$N($R^{66}$)$_2$, —N$R^{67}$SO$_2R^{66a}$, —SO$_3$H, —SO$_2R^{66a}$, —SO$_2$N($R^{66}$)$_2$, —N($R^{66}$)$_2$, and —OCH$_2$CO$_2$H;

$R^{66}$, $R^{66a}$, and $R^{67}$ are each independently selected at each occurrence from the group consisting of: hydrogen and $C_1$–$C_6$ alkyl;

n is 0 or 1;

and a, b, c, d, e and f indicate the positions of optional double bonds, provided that one of e and f.

10. The kit of claim 9, wherein:

$A_{L1}$ is a functionalized aminocarboxylate;

Q is a biologically active molecule selected from the group consisting of: IIb/IIIa receptor antagonists, IIb/IIIa receptor ligands, fibrin binding peptides, leukocyte binding peptides, chemotactic peptides, somatostatin analogs, and selectin binding peptides;

d' is 1 to 3;

$L_n$ is:

g" is 0–5;

f is 0–5;

f' is 1–5;

$Y^1$ and $Y^2$, at each occurrence, are independently selected from the group consisting of: O, N$R^{56}$, C=O, C(=O)O, OC(=O)O, C(=O)NH, C=N$R^{56}$, S, SO, SO$_2$, SO$_3$, NHC(=O), (NH)$_2$C(=O), and (NH)$_2$C=S;

$R^{55}$ and $R^{56}$ are independently selected at each occurrence from the group consisting of: hydrogen; $C_1$–$C_{10}$ alkyl and alkaryl;

$R^{40}$ is independently selected at each occurrence from the group consisting of: aryl substituted with 0–3 $R^{52}$, and heterocycle substituted with 0–3 $R^{52}$;

$R^{41}$ is independently selected from the group consisting of: hydrogen, aryl substituted with 0–1 $R^{52}$, $C_1$–$C_3$ alkyl substituted with 0–1 $R^{52}$, and a heterocycle substituted with 0–1 $R^{52}$;

$R^{52}$ is independently selected at each occurrence from the group consisting of: a bond to $L_n$, —CO$_2R^{53}$, —CH$_2$O$R^{53}$, —SO$_3$H, —SO$_2R^{53a}$, —N($R^{53}$)$_2$, —N($R^{53}$)$_3^+$, —NHC(=NH)NH$R^{53}$, and —OCH$_2$CO$_2$H;

$R^{53}$ and $R^{53a}$ are each independently selected at each occurrence from the group consisting of: hydrogen and $C_1$–$C_3$ alkyl;

$R^{80}$ is independently selected at each occurrence from the group consisting of: —$CO_2R^{85}$, $C_2$-$C_5$ 1-alkene substituted with 0–3 $R^{84}$, $C_2$-$C_5$ 1-alkyne substituted with 0–3 $R^{84}$, aryl substituted with 0–3 $R^{84}$, and unsaturated heterocycle substituted with 0–3 $R^{84}$;

$R^{81}$ is independently selected at each occurrence from the group consisting of: H and $C_1$-$C_5$ alkyl;

alternatively, $R^{80}$ and $R^{81}$, may be taken together with the shown divalent carbon radical to form:

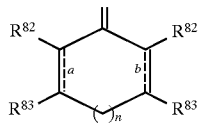

$R^{82}$ and $R^{83}$ may be independently selected from the group consisting of: H and $R^{84}$;

alternatively, $R^{82}$, $R^{83}$ may be taken together to form a fused aromatic or heterocyclic ring;

$R^{84}$ is independently selected at each occurrence from the group consisting of: —$CO_2R^{85}$, —$C(=O)N(R^{85})_2$, —$CH_2OR^{85}$, —$OC(=O)R^{85}$, —$OR^{85}$, —$SO_3H$, —$N(R^{85})_2$, and —$OCH_2CO_2H$;

$R^{85}$ is independently selected at each occurrence from the group consisting of: hydrogen and $C_1$-$C_3$ alkyl.

Y is $BR^{64-}$;

$R^{64}$ is independently selected at each occurrence from the group consisting of: H, $C_1$-$C_3$ alkyl substituted with 0–3 $R^{65}$, aryl substituted with 0–3 $R^{65}$ and $R^{65}$;

alternatively, two $R^{64}$ may be taken together with the atom or atoms to which they are attached to form a fused aromatic, or heterocyclic ring, substituted with 0–3 $R^{65}$;

$R^{65}$ is independently selected at each occurrence from the group consisting of: —$NO_2$, —$CO_2R^{66}$, —$OR^{66}$, —$SO_3H$, and —$OCH_2CO_2H$;

$R^{66}$ is hydrogen; and, n is 0.

11. The kit of claim 9, wherein:

$A_{L1}$ is a tricine;

Q is a biologically active molecule selected from the group consisting of: IIb/IIIa receptor antagonists, and chemotactic peptides;

d' is 1;

$Y^1$ and $Y^2$, at each occurrence, are independently selected from the group consisting of: O, $NR^{56}$, C=O, C(=O)O, OC(=O)O, C(=O)NH, C=$NR^{56}$, NHC(=O), and $(NH)_2C(=O)$;

$R^{55}$ and $R^{56}$ are hydrogen;

$R^{40}$ is heterocycle substituted with $R^{52}$;

$R^{41}$ is hydrogen;

$R^{52}$ is a bond to $L_n$;

$R^{80}$ is independently selected at each occurrence from the group consisting of: —$CO_2R^{85}$, $C_2$-$C_3$ 1-alkene substituted with 0–1 $R^{84}$, aryl substituted with 0–1 $R^{84}$, and unsaturated heterocycle substituted with 0–1 $R^{84}$;

$R^{81}$ is H;

$R^{84}$ is independently selected at each occurrence from the group consisting of: —$CO_2R^{85}$, —$OR^{85}$, —$SO_3H$, and —$N(R^{85})_2$;

$R^{85}$ is independently selected at each occurrence from the group consisting of: hydrogen and methyl;

$X^1$ is independently selected at each occurrence from the group consisting of: $CR^{64}$ and N;

$X^2$ is independently selected at each occurrence from the group consisting of: $CR^{64}$, $CR^{64}R^{64}$, N, $NR^{64}$, and O;

$X^3$ is N;

Y is $BR^{64-}$;

provided the total number of heteroatoms in each ring of the ligand $A_{L2}$ is 2 to 3;

$R^{64}$ is independently selected at each occurrence from the group consisting of: H, $C_1$-$C_3$ alkyl substituted with 0–1 $R^{65}$, aryl substituted with 0–1 $R^{65}$, and $R^{65}$;

$R^{65}$ is independently selected at each occurrence from the group consisting of: —$NO_2$, —$CO_2R^{66}$, $OR^{66}$, and —$SO_3H$;

$R^{66}$ is hydrogen;

n is 0;

and a, b, c, d, e and f indicate the positions of optional double bonds, provided that one of e and f is a double bond.

12. The kit of claim 9, wherein:

$A_{L2}$ is selected from the group consisting of:

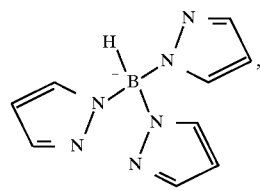

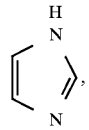

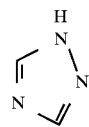

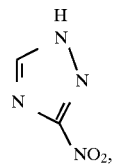

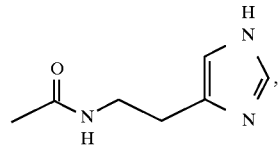

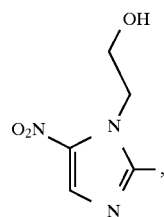

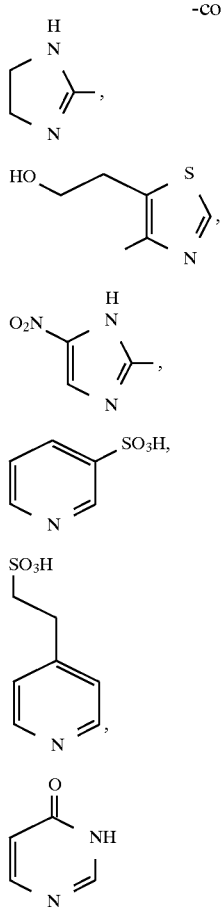

and

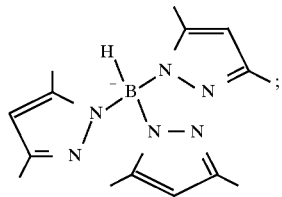

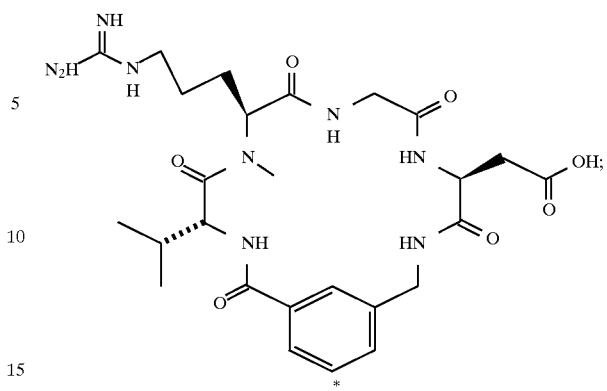

Q is d' is 1;

$L_n$ is attached to Q at the carbon atom designated with a * and has the formula:

—(C=O)NH(CH$_2$)$_5$C(=O)NH—;

$C_h$ is selected from $R^{40}NNH_2$— and $R^{40}R^{41}N$—N=$CR^{80}R^{81}$;

$R^{40}$ is independently heterocycle substituted with $R^{52}$;

$R^{41}$ is hydrogen;

$R^{52}$ is a bond to $L_n$;

$R^{80}$ is independently selected at each occurrence from the group consisting of: —CO$_2$R$^{85}$, C$_2$-C$_3$ 1-alkene substituted with 0–1 $R^{84}$, aryl substituted with 0–1 $R^{84}$ and unsaturated heterocycle substituted with 0–1 $R^{84}$;

$R^{81}$ is H;

$R^{84}$ is independently selected at each occurrence from the group consisting of: —CO$_2$R$^{85}$, —OR$^{85}$, —SO$_3$H, and —N(R$^{85}$)$_2$; and, $R^{85}$ is independently selected at each occurrence from the group consisting of: hydrogen and methyl.

* * * * *